United States Patent [19]

Tanaka et al.

[11] Patent Number: 5,656,578
[45] Date of Patent: Aug. 12, 1997

[54] MONOCARBONATES, USE THEREOF AND PROCESS FOR THE PREPARATION OF COMPOSITIONS CONTAINING MONOCARBONATES

[75] Inventors: Masahide Tanaka; Tetsuo Hayashi; Takashi Hayashi, all of Yamaguchi-ken; Kinya Mizui; Kunihiko Takeuchi, both of Ichihara; Hajime Oyoshi, Yamaguchi-ken, all of Japan

[73] Assignee: Mitsui Petrochemical Industries, Ltd., Tokyo, Japan

[21] Appl. No.: 619,881

[22] Filed: Mar. 20, 1996

[30] Foreign Application Priority Data

Mar. 24, 1995 [JP] Japan .................................. 7-066451

[51] Int. Cl.$^6$ ............................................. C10M 129/84
[52] U.S. Cl. ............................ 508/462; 252/68; 558/275
[58] Field of Search ............................ 508/462; 252/68; 558/275

[56] References Cited

U.S. PATENT DOCUMENTS

| Re. 34,914 | 4/1995 | Mizui et al. | 508/462 |
|---|---|---|---|
| 5,384,056 | 1/1995 | Tanaka et al. | 508/462 |
| 5,569,408 | 10/1996 | Peppmaller et al. | 508/462 |

*Primary Examiner*—Jacqueline V. Howard
*Attorney, Agent, or Firm*—Sherman and Shalloway

[57] ABSTRACT

A monocarbonate represented by the formula $(R^1)_n Ph-O(R^2O)_m-CO-O-CH_2-C(R^3)(R^4)(R^5)$, a lubricating oil containing this monocarbonate, and a process for preparing a composition of this monocarbonate, a monocarbonate to which are bonded, via carbonic acid, two $(R^5)(R^4)(R^3)C-CH_2-$ groups and a monocarbonate to which are bonded, via carbonic acid, two $(R^1)_n Ph-(OR^2)_m-$ groups. The monocarbonate exhibits excellent lubricating property, cleaning property and electrically insulating property, exhibits excellent compatibility with hydrogenated fluorocarbons such as R-134a, and can be favorably used as a lubricating oil for refrigerators such as electric refrigerators and air conditioners for room.

10 Claims, No Drawings

MONOCARBONATES, USE THEREOF AND PROCESS FOR THE PREPARATION OF COMPOSITIONS CONTAINING MONOCARBONATES

BACKGROUND OF THE INVENTION

1. Field of the Invention

The present invention relates to novel monocarbonates and their use, as well as to a process for the preparation of compositions containing the monocarbonates. More specifically, the invention relates to monocarbonates having carbonate bond that is protected and is little decomposed, to lubricating oils having excellent lubricating property, cleaning property and electrically insulating property that can be used as gear oils for industrial use, engine oils for automobiles, gear oils for automobiles, lubricating oils for refrigerators, lubricating oils for rolling and lubricating oils for fibers, for which strict lubricating property and cleaning property have heretofore been required, and, particularly, to lubricating oils that can be best used for the refrigerators that use, as a cooling medium, ozone layer non-depleting hydrogenated fluorocarbons (HFC) such as R-134a, as well as to a process for the preparation of compositions containing monocarbonates.

2. Prior Art

Lubricating oils include gear oils for industrial applications, engine oils, lubricating oils for fibers, lubricating oils for rolling, lubricating oils for refrigerators, traction oils and the like oils.

As it has now been urged to operate industrial machinery under ever severe conditions, it has been demanded to produce gear oils for industrial use that are capable of maintaining lubricating property and cleaning property up to high temperature ranges. In a step of baking finish and a step of baking foods, in particular, higher performance is required in regard to lubricating property and cleaning property. For such applications, there have heretofore been used lubricating oils of the types of synthetic hydrocarbons, carboxylic esters and glycols.

However, the synthetic hydrocarbon oils and carboxylic ester oils are not still satisfactory in regard to lubricating property, form carbonized materials after heated for extended periods of time, and are not capable of playing the role of lubricating oils under high-temperature conditions. On the other hand, the glycol lubricating oils have a merit of forming carbonized materials in small amounts even after heated for extended periods of time but have insufficient lubricating property and strong hygroscopic property, leaving room for improvement in regard to lubricating property and hygroscopic property.

Accompanying the trend toward producing automotive engines of higher performance, furthermore, it has been urged to produce engine oils that maintain lubricating property, cleaning property and dispersing property at higher temperatures even after used for longer periods of time. If it is attempted to meet such demands by selecting additives, the additives are inevitably used in large amounts bringing about a harmful effect, i.e., sedimentation of a mayonnaise sludge. It has heretofore been attempted to use a mineral oil as a base oil together with the synthetic hydrocarbon oil or the carboxylic ester oil without, however, satisfactory results in regard to lubricating property, cleaning property and dispersing property when used at high temperatures for extended periods of time.

Unlike the lubricating oils for the automotive engines, i.e., for the four-cycle engines, on the other hand, the lubricating oils for the two-cycle engines are burned being added to the gasoline and, hence, its cleaning property is most important. Castor oils and polybutenes have heretofore been used as lubricating oils for the two-cycle engines, but their lubricating property and cleaning property are not still satisfactory.

Gear oils for automobiles and, particularly, gear oils for ATF must have small coefficients of friction and must be aged little. Therefore, there have heretofore been used a friction-reducing agent and a friction-adjusting agent. However, gear oils for automobiles containing these additives still have a problem in that their coefficients of friction change greatly with the passage of time.

So far, lubricating oils of the types of carboxylic ester and glycol have been used for the fibers satisfying, however, neither lubricating property nor cleaning property.

A lubricating oil consisting of beef tallow has long been used for the rolling. This lubricating oil features excellent lubricating property and rolling efficiency but has very poor cleaning property, making it necessary to carry out the step of cleansing the beef tallow. Moreover, a lubricating oil of the type of carboxylic ester has been used for the rolling featuring very good cleaning property but low practicability because of its poor lubricating property.

In the refrigerators in which ozone layer non-depleting hydrogenated fluorocarbons such as R-134a ($CH_2F\text{---}CF_3$) have now been used as the coolant gas, mineral oils and alkylbenzene compounds that were used as lubricating oils are now no longer usable because they lack compatibility with the coolant gas. At present, a glycol ether lubricating oil has been developed for lubricating the refrigerators that use R-134a as the coolant gas.

U.S. Pat. No. 4,755,316 discloses a composition for compression refrigerators, comprising a tetrafluoroethane and a polyoxyalkylene glycol having a molecular weight of 300 to 2,000 and a dynamic viscosity of about 25 to 150 cst at 37° C.

However, the glycol ether lubricating oils have insufficient heat stability, strong hygroscopic property and cause rubber sealing members such as of NBR to shrink and hardened.

In modern refrigerators for car air conditioners, furthermore, there has been employed a through-vane type rotary compressor featuring both reduced size and increased efficiency. The lubricating oil for the through-vane type rotary compressor must have a large viscosity from the standpoint of sealing property and wear resistance. However, compounds having a glycol ether structure are not utilizable since they exhibit poor compatibility with respect to the ozone layer non-depleting hydrogenated fluorocarbons such as R-134a, when their molecular weights are increased to exhibit increased viscosities. This problem holds not only for the ozone layer non-depleting hydrogenated fluorocarbons but also for the hydrogenated chlorofluorocarbons (HCFC) having a small ozone depletion potential and for a mixture of the hydrogenated fluorocarbons and hydrogenated chlorofluorocarbons. Examples of the hydrogenated fluorocarbons include R-152a ($CHF_2\text{---}CH_3$), R-125 ($CHF_2\text{---}CF_3$) and R-32 ($CH_2F_2$) in addition to the above-mentioned R-134a. Examples of the hydrogenated chlorofluorocarbons include R-22 ($CHClF_2$), R-123 ($CHCl_2CF_3$) and R-124 ($CHClF\text{---}CF_3$).

In recent years, furthermore, carboxylic ester lubricating oils called polyol ester and hindered ester have been developed for lubricating the refrigerators that use hydrogenated fluorocarbons as the coolant. However, these lubricating oils form carboxylic acid upon the hydrolysis or the thermal decomposition resulting in the occurrence of corrosion and wear of metals or copper-plating phenomenon in the refrigerators due to the carboxylic acid. Therefore, these lubricating oils bring about a problem concerning the durability of the refrigerators.

There has also been developed a polycarbonate lubricating oil for lubricating the refrigerators that use hydrogenated fluorocarbons as the coolant, involving, however, a problem in that carbonic acid gas evolves due to the thermal decomposition and hydrolysis. The carbonic acid gas is not condensed in an ordinary refrigerator system which uses the hydrogenated fluorocarbons as the coolant and is not desirable since it deteriorates the refrigeration efficiency and rises the temperature in the step of compression.

As for the traction oils, alicyclic hydrocarbons have heretofore been studied as the operation fluids for the traction drive without, however, satisfactory results with respect to traction performance and durability.

SUMMARY OF THE INVENTION

Object of the Invention

The present invention is to solve the above-mentioned problems inherent in the prior art, and its object is to provide monocarbonates having excellent lubricating property, cleaning property, electrically insulating property and compatibility with respect to ozone layer non-depleting hydrogenated fluorocarbons, and having particularly high heat stability to suppress evolution of carboxylic acid and carbonic acid gas, to provide lubricating oils containing monocarbonates and to provide a process for the preparation of compositions containing monocarbonates.

BRIEF DESCRIPTION OF THE INVENTION

A novel monocarbonate of the present invention is represented by the following general formula [I]

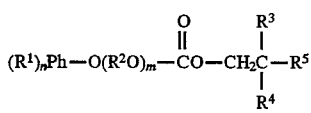

[I]

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, $R^3$, $R^4$ and $R^5$, which may be same or different, stands for a hydrocarbon group having 1 to 20 carbon atoms, an alkoxyl group having 1 to 12 carbon atoms or an etheric oxygen-containing hydrocarbon group having 2 to 20 carbon atoms, Ph stands for an Aromatic substituent, n stands for an integer of from 1 to 5, and m stands for an integer of from 1 to 30.

A first lubricating oil according to the present invention may contain, in addition to the monocarbonate represented by the above-mentioned general formula [I], a monocarbonate represented by the following general formula [II]

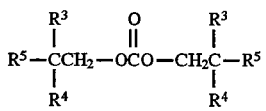

[II]

wherein $R^3$, $R^4$ and $R^5$, which may be same or different, stands for a hydrocarbon group having 1 to 20 carbon atoms, an alkoxyl group having 1 to 12 carbon atoms or an etheric oxygen-containing hydrocarbon group having 2 to 20 carbon atoms.

The first lubricating oil according to the present invention may further contain, in addition to the monocarbonate represented by the above-mentioned general formula [I] and the monocarbonate represented by the general formula [II], a monocarbonate represented by the following general formula [III],

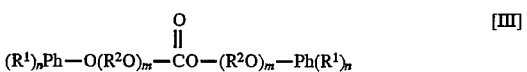

[III]

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands each independently for an aromatic substituent, n stands each independently for an integer of from 1 to 5, and m stands each independently for an integer of from 1 to 30.

A second lubricating oil according to the present invention contains the monocarbonate represented by the above-mentioned general formula [II] and the monocarbonate represented by the general formula [III].

According to the present invention, there is provided a process for the preparation of a composition of the monocarbonate represented by the above-mentioned general formula [I], monocarbonate represented by the general formula [II] and monocarbonate represented by the general formula [III], comprising heating a mixture of:

(a) a monoalcohol having an aromatic ring represented by the general formula [IV]

[IV]

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands for an aromatic substituent, n stands for an integer of from 1 to 5, and m stands for an integer of from 1 to 30, (b) a monoalcohol represented by the general formula [V]

[V]

wherein $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 20 carbon atoms, and (c) a monocarbonate represented by the general formula [VI]

[VI]

wherein $R^6$ and $R^7$, which may be same or different, stands for a hydrocarbon group having 1 to 8 carbon atoms or an etheric oxygen-containing hydrocarbon group having 2 to 8 carbon atoms, and removing $R^6OH$ and/or $R^7OH$.

DETAILED DESCRIPTION OF THE INVENTION

Concretely described below are monocarbonates, lubricating oils containing monocarbonates and a process for the preparation of compositions containing monocarbonates according to the present invention.

First, a monocarbonate of the present invention will be described.

The monocarbonate according to the present invention is represented by the following general formula [I]

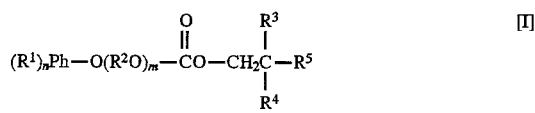

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 20 carbon atoms, Ph stands for an aromatic substituent, n stands for an integer of from 1 to 5, and m stands for an integer of from 1 to 30.

Concrete examples of the hydrocarbon group having 1 to 20 carbon atoms represented by $R^1$ in the above-mentioned general formula [I] include methyl group, ethyl group, n-propyl group, isopropyl group, n-butyl group, isobutyl group, s-butyl group, t-butyl group, n-pentyl group, isopentyl group, neopentyl group, n-hexyl group, 2,3-dimethylbutyl group, isohexyl group, n-heptyl group, isoheptyl group, n-octyl group, 2-ethylhexyl group, isooctyl group, n-nonyl group, isononyl group, n-decyl group, isodecyl group, n-undecyl group, isoundecyl group, n-dodecyl group, isododecyl group, isotridecyl group, isotridecyl group, n-tetradecyl group, isotetradecyl group, n-pentadecyl group, isopentadecyl group, n-hexadecyl group, isohexadecyl group, n-heptadecyl group, isopentadecyl group, n-octadecyl group, isooctadecyl group, n-nonyldecyl group, isononyldecyl group, n-icosanyl group, isoicosanyl group, 2-(4-methylpentyl) group and the like groups.

As the alkoxyl group having 1 to 12 carbon atoms represented by $R^1$, furthermore, there can be concretely exemplified methoxy group, ethoxy group, propoxy group, butoxy group, hexyloxy group and the like groups.

Moreover, concrete examples of the etheric oxygen-containing hydrocarbon group having 2 to 30 carbon atoms represented by $R^1$ include ethylene glycol monomethyl ether group, ethylene glycol monoethyl ether group, ethylene glycol monopropyl ether group, ethylene glycol monobutyl ether group, diethylene glycol monomethyl ether group, diethylene glycol monoethyl ether group, diethylene glycol monobutyl ether group, triethylene glycol monomethyl ether group, propylene glycol monomethyl ether group, propylene glycol monopropyl ether group, propylene glycol monobutyl ether group, dipropylene glycol monomethyl ether group, dipropylene glycol monopropyl ether group, dipropylene glycol monobutyl ether group, tripropylene glycol monomethyl ether group, butylene glycol monomethyl ether group, butylene glycol monobutyl ether group and the like groups.

As the halogen-substituted hydrocarbon group having 1 to 10 carbon atoms represented by $R^1$, there can be concretely exemplified $Cl_3C$— group, $Cl_2HC$— group, $ClH_2C$— group, $CF_3$— group, $FCH_2$— group, $HCF_2CH_2$— group, $HCF_2CF_2CH_2O$— group, $CF_3CH_2$— group, $H(C_2F_4)$— group, $H(C_2F_4)_2O$— group, $H(C_2F_4)_3O$— group, $CF_3CHFCF_2O$— group and the like groups.

As the alkylene group represented by $R^2$ in the general formula [I], there can be concretely exemplified ethylene group, propylene group and butylene group.

Concrete examples of hydrocarbon groups having 1 to 20 carbon atoms represented by $R^3$, $R^4$ and $R^5$ include aliphatic hydrocarbon groups such as methyl group, ethyl group, n-propyl group, isopropyl group, n-butyl group, isobutyl group, s-butyl group, t-butyl group, n-pentyl group, isopentyl group, neopentyl group, n-hexyl group, 2,3-dimethylbutyl group, isohexyl group, n-heptyl group, isoheptyl group, n-octyl group, 2-ethylhexyl group, isooctyl group, 1,1,3,3-tetramethyl butyl group, n-nonyl group, isononyl group, n-decyl group, isodecyl group, n-undecyl group, isoundecyl group, n-dodecyl group, isododecyl group, n-tridecyl group, isotridecyl group, n-tetradecyl group, isotetradecyl group, n-pentadecyl group, isopentadecyl group, n-hexadecyl group, isohexadecyl group, n-heptadecyl group, isopentadecyl group, n-octadecyl group, isooctadecyl group, n-nonyldecyl group, isononyldecyl group, n-icosanyl group, isoicosanyl group, 2-ethylhexyl group, 2-(4-methylpentyl) group and the like groups; alicyclic hydrocarbon groups such as cyclohexyl group, 1-cyclohexenyl group, methylcyclohexyl group, dimethylcyclohexyl group, 1-ethyl-1-cyclohexyl group, decahydronaphthyl group, tricyclodecanyl group and the like groups; and aromatic hydrocarbon groups such as phenyl group, o-tolyl group, p-tolyl group, m-tolyl group, 2,4-xylyl group, mesityl group, p-t-butylphenyl group, p-t-amylphenyl group, p-octylphenyl group, p-nonylphenyl group, p-dodecaphenyl group, o,p-di-t-butylphenyl group, o,p-di-t-amylphenyl group, benzyl group, α,α'-dimethylbenzyl group, methylbenzyl group, β-phenylethyl group (phenetyl group), 1-phenylethyl group, 1-methyl-1-phenylethyl group, p-methylbenzyl group, styryl group, cinnamyl group and the like groups.

Concrete examples of the alkoxyl groups having 1 to 12 carbon atoms represented by $R^3$, $R_4$ and $R^5$ will be those groups that were concretely exemplified as the alkoxyl groups having 1 to 12 carbon atoms represented by $R^1$.

As the etheric oxygen-containing hydrocarbon groups having 2 to 20 carbon atoms represented by $R^3$, $R^4$ and $R^5$, there can be exemplified the groups represented by the following general formula [VII]

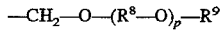

wherein $R^8$ stands for an alkylene group having 1 to 4 carbon atoms, $R^9$ stands for a hydrocarbon group having 1 to 19 carbon atoms, and p stands for an integer of from 1 to 9.

Concrete examples of the alkylene group $R^8$ include methylene group, ethylene group, propylene group, butylene group and the like groups.

Concrete examples of the hydrocarbon group $R^9$ include aliphatic hydrocarbon groups, alicyclic hydrocarbon groups and aromatic hydrocarbon groups, which are those that were concretely described above as the examples of aliphatic hydrocarbon groups, alicyclic hydrocarbon groups and aromatic hydrocarbon groups represented by $R^3$, $R^4$ and $R^5$.

Concrete examples of the group Ph include phenylene group and the like groups.

Examples of the monocarbonate represented by the general formula [I] include the following ones:

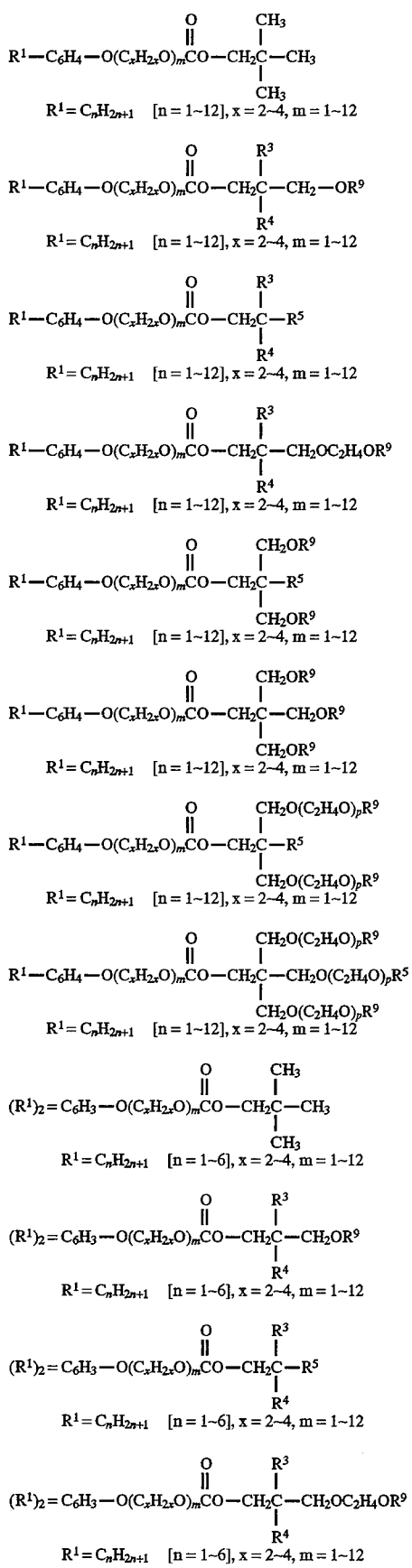

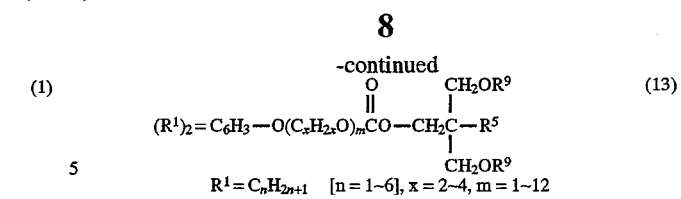

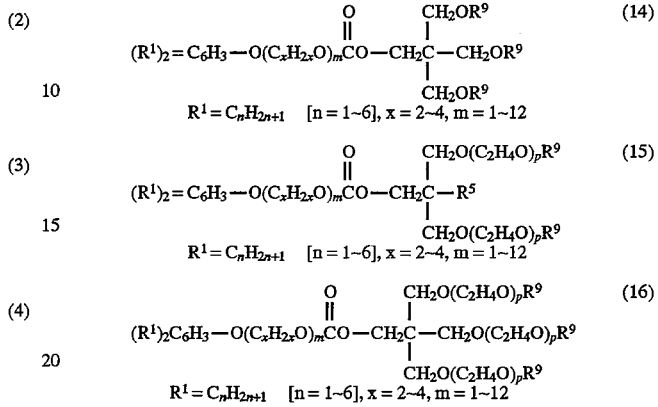

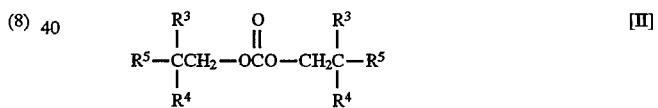

(17) to (24) are monocarbonates represented by the same formulae as (1) to (8) except that $R^1$ in the formular is a $CH_3O-$ group.

(25) to (32) are monocarbonates in which $R^1$ in the above-mentioned formulas (1) to (8) is a $CF_3-$ group.

In the above-mentioned formulas (1) to (32), the groups $R^3$, $R^4$ and $R^5$ are the same as the groups $R^3$, $R^4$ and $R^5$ in the above-mentioned general formula [I]. Furthermore, the group $R^9$ is the same as the group $R^9$ in the above-mentioned general formula [VII], and p is the same as p in the above-mentioned general formula [VII].

The monocarbonate represented by the above-mentioned general formula [I] can be prepared by, for example, a process mentioned below. That is, the desired monocarbonate represented by the general formula [I] is obtained by heating a mixture of (a) a monocarbonate represented by the general formula [II]

$$\begin{array}{c} R^3 \quad O \quad R^3 \\ | \quad \| \quad | \\ R^5-CCH_2-OCO-CH_2C-R^5 \\ | \qquad\qquad\qquad | \\ R^4 \qquad\qquad\qquad R^4 \end{array} \qquad [II]$$

wherein $R^3$, $R^4$ and $R^5$ which may be same or different, stand for a hydrocarbon group having 1 to 20 carbon atoms, an alkoxyl group having 1 to 12 carbon atoms or an etheric oxygen-containing hydrocarbon group having 2 to 20 carbon atoms, and (b) a monoalcohol containing an aromatic ring represented by the general formula [IV]

$$(R^1)_n Ph-O(R^2O)_m H \qquad [IV]$$

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands for an aromatic substituent, n stands for an integer of from 1 to 5, and m stands for an integer of from 1 to 30, in the presence of a basic catalyst, and distilling monoalcohol that is formed off the reaction system.

In heating the mixture, it is desired to substitute the air in the reactor with nitrogen. The air, however, needs not always be substituted with nitrogen.

Concrete examples of the aromatic ring-containing monoalcohol (b) represented by the general formula [IV] include the following compounds:

(1) $R^1$—$C_6H_4$—$O(C_xH_{2x}O)_m$—H [$R^1$=$C_nH_{2n+1}$ (n=1 to 12), x=2 to 4, m=1 to 12]

(2) $(R^1)_2$=$C_6H_3$—$O(C_xH_{2x}O)_m$—H [$R^1$=$C_nH_{2n+1}$ (n=1 to 6), x=2 to 4, m=1 to 12]

(3) $CH_3O$—$C_6H_4$—$O(C_xH_{2x}O)_m$—H [x=2 to 4, m=1 to 12]

(4) $CF_3$—$C_6H_4$—$O(C_xH_{2x}O)_m$—H [x=2 to 4, m=1 to 12]

In the above-mentioned compounds (1) to (4), $C_nH_{2n-1}$ and $C_xH_{2x}O$ may be straight chains or branched chains.

Examples of the basic catalyst include alkali metal hydroxides such as sodium hydroxide, potassium hydroxide, etc.; alkali metal carbonates and hydrogen carbonates such as sodium carbonate, sodium hydrogencarbonate, etc.; alkali metal alcoholates such as sodium methoxide, potassium methoxide, lithium methoxide, cesium methoxide, etc.; and alkali metal compounds such as sodium hydride, sodium amide, etc. Among them, it is particularly desired to use an alkali metal alcoholate. There can be further used alkaline earth metal compounds such as magnesium hydroxide, calcium hydroxide, etc., and organic amino compounds such as trimethylamine, triethylamine, imidazole, tetramethylammonium hydroxide, etc. These catalysts are used usually in such amounts that the mol number of the catalyst/mol number of the aromatic ring-containing monoalcohol (b) (mol ratio) is from 1 to $10^{-7}$ and, preferably, from $10^{-1}$ to $10^{-5}$.

In this process, the reaction is carried out at a temperature of usually from 50° to 300° C. and, preferably, from 60° to 200° C. The reaction time is usually from 0.1 to 100 hours and, preferably, from 0.5 to 30 hours.

The monocarbonate represented by the general formula [I] obtained as described above features excellent cleaning property and lubricating property, has a volume resistivity of the order of $10^{13}$ to $10^{14}$Ω·cm and exhibits a higher electrically insulating property than that of the conventional polyether lubricating oils. As is obvious from the above-mentioned general formula [I], furthermore, the monocarbonate has a structure which is substituted with many alkyl groups, and exhibits excellent resistance against hydrolysis, does not form carboxylic acid unlike the carboxylic ester lubricating oils, and does not cause the machine to be corroded with carboxylic acid. Therefore, the monocarbonate can be desirably used as the lubricating oil and as the electrically insulating oil that requires electrically insulating property.

Moreover, the lubricating oil containing monocarbonate of the structure substituted with many alkyl groups of the present invention is capable of suppressing the evolution of carbonic acid gas caused by the decomposition of carbonate compound compared with the conventional polycarbonate-containing lubricating oils.

Therefore, the lubricating oil of the present invention can be extensively used as a lubricating oil for refrigerators such as of car air conditioners, electric refrigerators, air conditioners for room, as a gear oil for industrial uses, as an automobile engine oil, as an automobile gear oil, as a lubricating oil for fibers, as a lubricating oil for rolling and as a traction oil.

Moreover, the lubricating oil of the present invention exhibits not only excellent properties as described above but also excellent compatibility with the ozone layer non-depleting hydrogenated fluorocarbons (HFC) such as R-134a. Furthermore, the lubricating oil according to the present invention exhibits excellent compatibility with the hydrogenated chlorofluorocarbons (HCFC) such as R-22 having less ozone depletion potential and even with a mixture of the hydrogenated fluorocarbons and the hydrogenated chlorofluorocarbons. Therefore, the lubricating oil of the present invention can be favorably used for the refrigerators such as electric refrigerators and air conditioners for room that use, as a coolant, the hydrogenated fluorocarbons, hydrogenated chlorofluorocarbons or a mixture thereof.

Examples of the monocarbonate represented by the general formula [I] that can be favorably used as a lubricating oil for the refrigerators for the air conditioners for room include the following compounds.

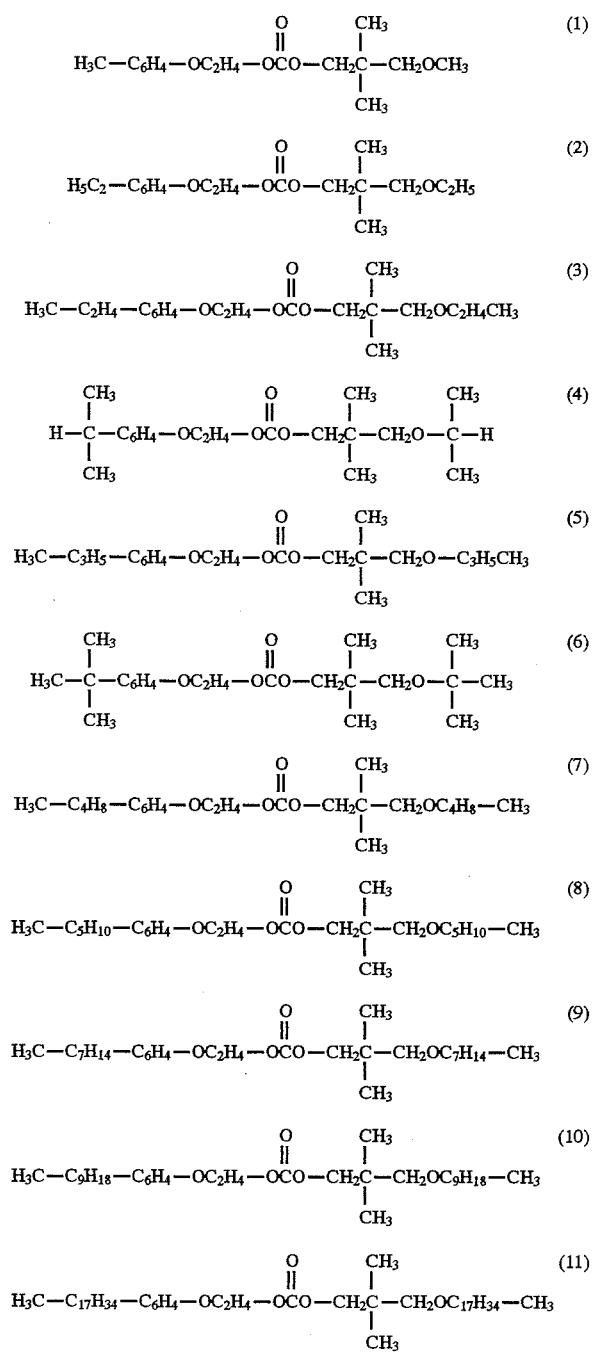

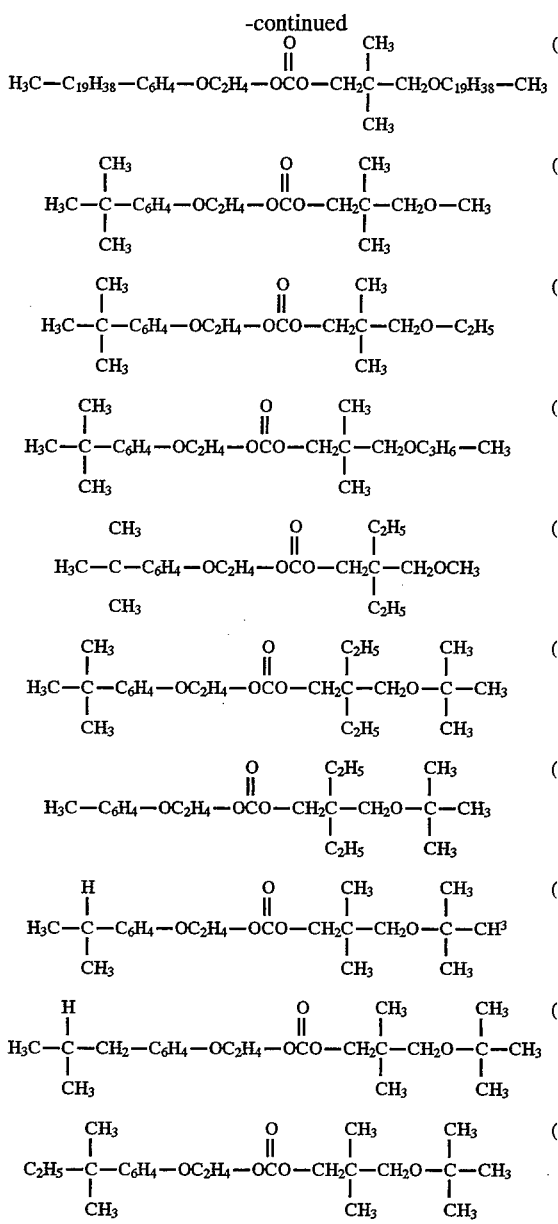

The lubricating oil of the present invention may further contain a monocarbonate represented by the following general formula [II]

$$R^5-\underset{\underset{R^4}{|}}{\overset{\overset{R^3}{|}}{C}}CH_2-OCO-CH_2\underset{\underset{R^4}{|}}{\overset{\overset{R^3}{|}}{C}}-R^5 \quad [II]$$

wherein $R^3$, $R^4$ and $R^5$ stand for the same groups as those of $R^3$, $R^4$ and $R^5$ of the general formula [I], in addition to the monocarbonate represented by the above-mentioned general formula [I].

Examples of the monocarbonate represented by the above general formula [II] include the following compounds:

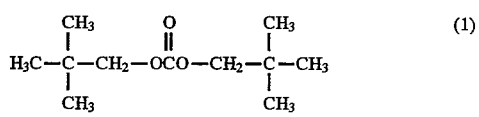

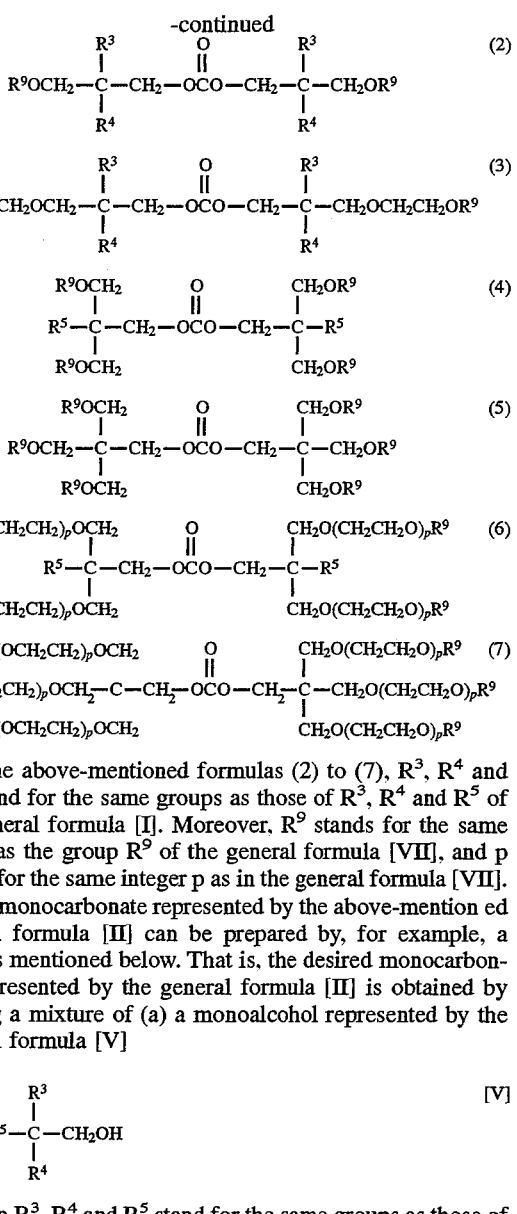

In the above-mentioned formulas (2) to (7), $R^3$, $R^4$ and $R^5$, stand for the same groups as those of $R^3$, $R^4$ and $R^5$ of the general formula [I]. Moreover, $R^9$ stands for the same group as the group $R^9$ of the general formula [VII], and p stands for the same integer p as in the general formula [VII].

The monocarbonate represented by the above-mention ed general formula [II] can be prepared by, for example, a process mentioned below. That is, the desired monocarbonate represented by the general formula [II] is obtained by heating a mixture of (a) a monoalcohol represented by the general formula [V]

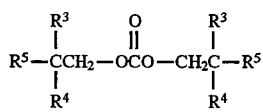

wherein $R^3$, $R^4$ and $R^5$ stand for the same groups as those of $R^3$, $R^4$ and $R^5$ in the above-mentioned general formula [II], and (b) a monocarbonate represented by the general formula [VI]

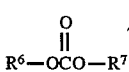

wherein $R^6$ and $R^7$, which may be the same or different, stand for a hydrocarbon group having 1 to 8 carbon atoms or an etheric oxygen-containing hydrocarbon group having 2 to 8 carbon atoms, in the presence of a basic catalyst, and distilling $R^6OH$ and/or $R^7OH$ that is formed and the unreacted monocarbonate represented by the above-mentioned general formula [VI] off the reaction system.

In heating the mixture, it is desired to substitute the air in the reactor with nitrogen. The air, however, needs not always be substituted with nitrogen.

Concrete examples of the monoalcohol (a) represented by the above-mentioned general formula [V] include the following compounds:

$CH_3—C(CH_3)_2—CH_2OH$,
$CH_3—C(C_2H_5)_2—CH_2OH$,
$CH_3—C(C_3H_7)_2—CH_2OH$,
$CH_3—C(C_4H_9)_2—CH_2OH$,
$C_2H_5—C(C_2H_5)_2—CH_2OH$,
$C_2H_5—C(CH_3)_2—CH_2OH$,
$C_2H_5—C(C_3H_7)_2—CH_2OH$,
$C_2H_5—C(C_4H_9)_2—CH_2OH$,
$C_3H_7—C(C_3H_7)_2—CH_2OH$,
$C_3H_7—C(C_2H_5)_2—CH_2OH$,
$C_3H_7—C(C_4H_9)_2—CH_2OH$,
$C_{10}H_{21}—C(C_{10}H_{21})_2—CH_2OH$,
$C_{19}H_{39}—C(C_{19}H_{39})_2—CH_2OH$,
$C_{20}H_{41}—C(C_{20}H_{41})_2—CH_2OH$,
$CH_3OCH_2—C(CH_3)_2—CH_2OH$,
$CH_3OCH_2—C(C_2H_5)_2—CH_2OH$,
$CH_3OCH_2—C(C_3H_7)_2—CH_2OH$,
$CH_3OCH_2—C(C_4H_9)_2—CH_2OH$,
$C_2H_5OCH_2—C(C_2H_5)_2—CH_2OH$,
$C_2H_5OCH_2—C(C_3H_7)_2—CH_2OH$,
$C_2H_5OCH_2—C(C_4H_9)_2—CH_2OH$,
$C_3H_7OCH_2—C(C_3H_7)_2—CH_2OH$,
$C_3H_7OCH_2—C(C_4H_9)_2—CH_2OH$,
$C_{10}H_{21}OCH_2—C(C_{10}H_{21})_2—CH_2OH$,
$C_{20}H_{41}OCH_2—C(C_{20}H_{41})_2—CH_2OH$,
$CH_3OCH_2CH_2OCH_2—C(CH_3)_2—CH_2OH$,
$CH_3OCH_2CH_2OCH_2—C(C_2H_5)_2—CH_2OH$,
$CH_3OCH_2CH_2OCH_2—C(C_3H_7)_2—CH_2OH$,
$C_2H_5OCH_2CH_2OCH_2—C(C_2H_5)_2—CH_2OH$,
$C_2H_5OCH_2CH_2OCH_2—C(C_3H_7)_2—CH_2OH$,
$C_3H_7OCH_2OCH_2—C(C_3H_7)_2—CH_2OH$,
$C_3H_7OCH_2CH_2OCH_2—C(C_4H_9)_2—CH_2OH$,
$CH_3—(C_2H_5)C(C_3H_7)—CH_2OH$,
$C_2H_5—(C_3H_7)C(C_4H_9)—CH_2OH$,
$C_3H_7—(C_4H_9)C(C_5H_{11})—CH_2OH$,
$C_{10}H_{21}—(C_{11}H_{23})C(C_{12}H_{25})—CH_2OH$,
$C_{18}H_{37}—(C_{19}H_{39})C(C_{20}H_{41})—CH_2OH$,
$CH_3OCH_2—(CH_3)C(C_2H_5)—CH_2OH$,
$CH_3OCH_2—(C_2H_5)C(C_3H_7)—CH_2OH$,
$CH_3OCH_2—(C_3H_7)C(C_4H_9)—CH_2OH$,
$CH_3OCH_2CH_2OCH_2—(CH_3)C(C_2H_5)—CH_2OH$,
$CH_3OCH_2CH_2OCH_2—(C_2H_5)C(C_3H_7)—CH_2OH$,
$C_2H_5OCH_2CH_2OCH_2—(C_2H_5)C(C_3H_7)—CH_2OH$,
$C_2H_5OCH_2CH_2OCH_2—(C_3H_7)C(C_4H_9)—CH_2OH$,
$C_3H_7OCH_2CH_2OCH_2—(C_3H_7)C(C_4H_9)_2—CH_2OH$,
$C_4H_9O—C(CH_3)_2—CH_2OH$,
$C_5H_{11}O—C(CH_3)_2—CH_2OH$,
$C_6H_{11}—O—C(CH_3)_2—CH_2OH$, (wherein $C_6H_{11}$—is a cyclohexyl group),
$C_6H_{11}—CH_2—O—C(CH_3)_2—CH_2OH$, (wherein $C_6H_{11}$—is a cyclohexyl group),
$C_6H_{10}(C_2H_5)—CH_2—O—C(CH_3)_2—CH_2OH$, (wherein $C_6H_{11}(C_2H_5)$— is a cyclohexyl group in which a hydrogen atom at a first position is substituted by an ethyl group),
$C_6H_5—CH_2—O—C(CH_3)_2—CH_2OH$, (wherein $C_6H_5$— is a phenyl group),
$C_8H_{17}—O—C(CH_3)_2—CH_2OH$,
$C_4H_9—O—C(C_2H_5)_2—CH_2OH$,
$C_6H_{11}—O—C(C_2H_5)_2—CH_2OH$, (wherein $C_6H_{11}$— is a cyclohexyl group),
$C_8H_{17}—O—C(C_2H_5)_2—CH_2OH$,
$C_4H_9—O—(C_2H_5)C(C_4H_9)—CH_2OH$,
$C_6H_{11}—O—CH_2—(C_2H_5)C(C_4H_9)—CH_2OH$, (wherein $C_6H_{11}$— is a cyclohexyl group),
$C_8H_{17}—O—CH_2—(C_2H_5)C(C_4H_9)—CH_2OH$,
$(C_4H_9OCH_2)_2=C(CH_3)—CH_2OH$,
$(C_4H_9OCH_2)_2=C(C_2H_5)—CH_2OH$,
$(C_4H_9OCH_2)_3C—CH_2OH$,
$(C_4H_9OCH_2CH_2OCH_2)_2=C(CH_3)$ - $CH_2OH$,
$(C_4H_9OCH_2CH_2OCH_2)_3C—CH_2OH$, Concrete examples of the monocarbonate (b) represented by the above-mentioned general formula [VI] include dimethyl carbonate, diethyl carbonate, dipropyl carbonate, dibutyl carbonate, dihexyl carbonate, di-2-ethylhexyl carbonate, dimethoxyethyl carbonate, $[CH_3OC_2H_4OC_2H_4O]_2CO$ and the like. Among them, it is desired to use the dimethyl carbonate.

The monoalcohol (a) represented by the above-mentioned general formula [V] wherein $R^3$, $R^4$ and $R^5$ are etheric oxygen-containing groups of the general formula [VII] can be synthesized by, for example, a process which is described below.

First, (c) an alcohol represented by the general formula [VIII]

$$[H(OR^3)_p—OCH_2]_q\overset{\underset{\textstyle |}{CH_2OH}}{C}(R^{10})_{3-q} \quad [VIII]$$

wherein $R^8$ and p are the same as $R^8$ and p of the above-mentioned general formula [VII], q stands for an integer of from 1 to 3, and $R^{10}$ is the same as $R^3$, $R^4$ or $R^5$ mentioned above and may be the same or different when it exists in a plural number, and (d) an olefin corresponding to $R^9$ having 1 to 19 carbon atoms represented by the above-mentioned general formula [VII], are reacted in the presence of an acid catalyst in order to add this olefin to the hydroxyl group of the general formula [VIII].

Next, the acid catalyst is filtered and, as required, is neutralized with an alkali. Then, the monoalcohol (a) represented by the above-mentioned general formula [V] is obtained by distillation.

The reaction time is from 0.1 to 300 hours, preferably, from 0.2 to 50 hours and, more preferably, from 1 to 10 hours, and the reaction temperature is from 0° to 300° C., preferably, from 10° to 100° C. and, more preferably, from 20° to 60° C.

Examples of the acid catalyst used for the above reaction include general inorganic acid, organic acid, acidic ion-exchange resin, solid acid and Lewis acid.

It is also allowable to use a solvent as required. The solvent is used in such an amount that the ratio of (weight of solvent)/(weight of alcohol (c)) is from 0.2 to 100 and, preferably, from 1 to 10. Any solvent can be used provided it does not adversely affect the reaction.

The mol ratio of the alcohol (c) to the olefin (d), i.e., [mol number of (d)]/[(mol number of (c))×(q+1)] is from 0.1 to 10, preferably, from 0.5 to 5, and more preferably, from 0.8 to 3.

Concrete examples of the above-mentioned basic catalyst are the same as the concrete examples of the basic catalyst used for the production of the monocarbonate represented by the above-mentioned general formula [I]. The catalyst is used usually in such an amount that the mol number of the catalyst/mol number of the monoalcohol (a) (mol ratio) is from $10^{-1}$ to $10^{-7}$ and, preferably, from $10^{-2}$ to $10^{-5}$.

In this process, the reaction is carried out usually at a temperature of from 50° to 300° C. and, preferably, from 60° to 200° C., and the reaction time is usually from 0.5 to 200 hours and, preferably, from 1 to 100 hours.

The monocarbonate represented by the general formula [II] obtained as described above exhibits excellent properties like the monocarbonate represented by the general formula [I].

Examples of the monocarbonate represented by the general formula [II] which is preferably used as a lubricating oil for the refrigerators of the air conditioners for room include the following compounds:

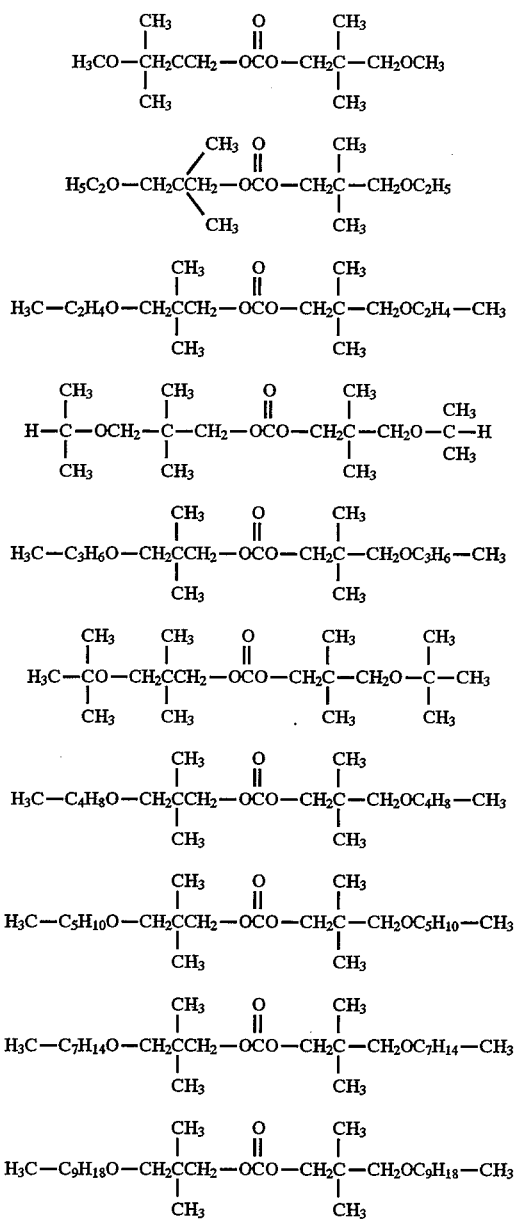

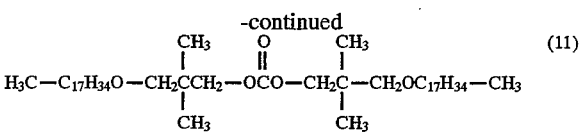

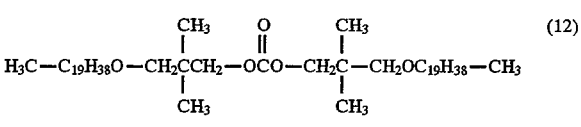

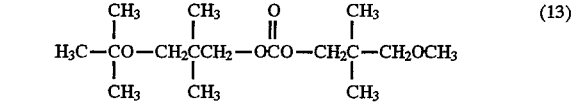

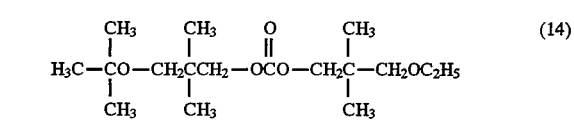

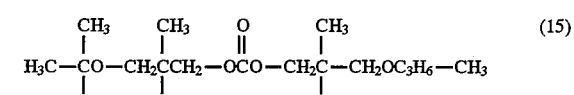

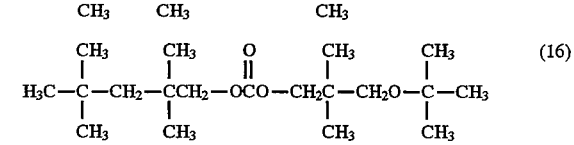

When the lubricating oil according to the present invention contains the monocarbonate represented by the general formula [I] and the monocarbonate represented by the general formula [II], the monocarbonate represented by the general formula [I] is used in an amount of from 98 to 5 parts by weight, preferably, from 95 to 10 parts by weight, and more preferably, from 90 to 30 parts by weight, and the monocarbonate represented by the general formula [II] is used in an amount of from 95 to 2 parts by weight, preferably, from 90 to 5 parts by weight, and more preferably, from 70 to 10 parts by weight per 100 parts by weight of the total of the two monocarbonates.

It is further allowable that the lubricating oil according to the present invention contains the monocarbonate represented by the following general formula [III] in addition to the monocarbonate represented by the general formula [I] and the monocarbonate represented by the general formula [II].

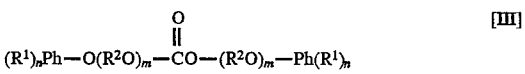

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands each independently for an aromatic substituent, n stands each independently for an integer of from 1 to 5, and m stands each independently for an integer of from 1 to 30.

Examples of the monocarbonate represented by the above-mentioned general formula [III] include the following compounds:

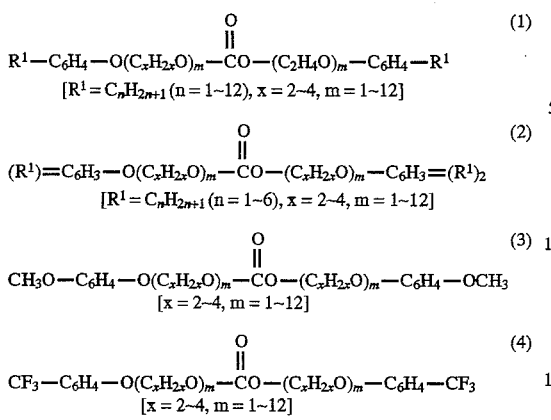

(1) $R^1$—$C_6H_4$—$O(C_xH_{2x}O)_m$—$CO$—$(C_2H_4O)_m$—$C_6H_4$—$R^1$
[$R^1 = C_nH_{2n+1}$ (n = 1~12), x = 2~4, m = 1~12]

(2) $(R^1) = C_6H_3$—$O(C_xH_{2x}O)_m$—$CO$—$(C_xH_{2x}O)_m$—$C_6H_3 = (R^1)_2$
[$R^1 = C_nH_{2n+1}$ (n = 1~6), x = 2~4, m = 1~12]

(3) $CH_3O$—$C_6H_4$—$O(C_xH_{2x}O)_m$—$CO$—$(C_xH_{2x}O)_m$—$C_6H_4$—$OCH_3$
[x = 2~4, m = 1~12]

(4) $CF_3$—$C_6H_4$—$O(C_xH_{2x}O)_m$—$CO$—$(C_xH_{2x}O)_m$—$C_6H_4$—$CF_3$
[x = 2~4, m = 1~12]

In the above-mentioned formulas (1) to (4), $C_nH_{2n+1}$ and $C_xH_{2x}O$ may be straight chains or branched chains.

The monocarbonate represented by the above-mentioned general formula [III] can be prepared by, for example, a process that is described below.

That is, the desired monocarbonate represented by the general formula [III] is obtained by heating a mixture of (a) a monoalcohol having an aromatic ring represented by the general formula [IV]

$(R^1)_n$Ph—O$(R^2O)_m$H     [IV]

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands for an aromatic substituent, n stands for an integer of from 1 to 5, and m stands for an integer of from 1 to 30, and (b) a monocarbonate represented by the general formula [VI]

$R^6$—OCO—$R^7$     [VI]

wherein $R^6$ and $R^7$, which may be same or different, stand for a hydrocarbon group having 1 to 8 carbon atoms or an etheric oxygen-containing hydrocarbon group having 2 to 8 carbon atoms, in the presence of a basic catalyst, and distilling the formed $R^6OH$ and/or $R^7OH$ and the unreacted monocarbonate represented by the general formula [VI] off the reaction system.

In heating the mixture, it is desired to substitute the air in the reactor with nitrogen. The air, however, needs not always be substituted with nitrogen.

Concrete examples of the aromatic ring-containing monoalcohol (a) represented by the above-mentioned general formula [IV] are as described above in connection with the preparation of the monocarbonate represented by the general formula [I].

Concrete examples of the monocarbonate (b) represented by the above-mentioned general formula [VI] are as described above in connection with the preparation of the monocarbonate represented by the general formula [III].

Concrete examples of the basic catalyst are the same as the concrete examples of the basic catalyst used for the preparation of the monocarbonate represented by the general formula [I]. The catalyst is used usually in such an amount that the mol number of the catalyst/mol number of the aromatic ring-containing monoalcohol (a) (mol ratio) is from $10^{-1}$ to $10^{-7}$ and, preferably, from $10^{-2}$ to $10^{-5}$.

According to this process, the reaction is carried out usually at a temperature of from 50° to 300° C. and, preferably, from 60° to 200° C. The reaction time is usually from 0.5 to 100 hours and, preferably, from 1 to 100 hours.

The monocarbonate represented by the general formula [III] obtained as described above exhibits excellent properties like the monocarbonate represented by the above-mentioned general formula [I].

Examples of the monocarbonate represented by the general formula [III] which is preferably used as a lubricating oil for the refrigerators of air conditioners for room include the following compounds:

(1) $H_3C$—$C_6H_4$—$OC_2H_4$—$OCO$—$C_2H_4O$—$C_6H_4$—$CH_3$ (2) $H_5C_2$—$C_6H_4$—$OC_2H_4$—$OCO$—$C_2H_4O$—$C_6H_4$—$C_2H_5$ (3) $H_3C$—$C_2H_4$—$C_6H_4$—$OC_2H_4$—$OCO$—$C_2H_4O$—$C_6H_4$—$C_2H_4$—$CH_3$ (4) $H_3C$—$\underset{\underset{}{}}{\overset{CH_3}{CH}}$—$C_6H_4$—$OC_2H_4$—$OCO$—$C_2H_4O$—$C_6H_4$—$\underset{}{\overset{CH_3}{CH}}$—$CH_3$ (5) $H_3C$—$C_3H_6$—$C_6H_4$—$OC_2H_4$—$OCO$—$C_2H_4O$—$C_6H_4$—$C_3H_5$—$CH_3$ (6) $H_3C$—$\underset{\underset{CH_3}{|}}{\overset{\overset{CH_3}{|}}{C}}$—$C_6H_4$—$OC_2H_4$—$OCO$—$C_2H_4O$—$C_6H_4$—$\underset{\underset{CH_3}{|}}{\overset{\overset{CH_3}{|}}{C}}$—$CH_3$ (7) $H_3C$—$C_4H_8$—$C_6H_4$—$OC_2H_4$—$OCO$—$C_2H_4O$—$C_6H_4$—$C_4H_8$—$CH_3$ (8) $H_3C$—$C_5H_{10}$—$C_6H_4$—$OC_2H_4$—$OCO$—$C_2H_4O$—$C_6H_4$—$C_5H_{10}$—$CH_3$ (9) $H_3C$—$C_7H_{14}$—$C_6H_4$—$OC_2H_4$—$OCO$—$C_2H_4O$—$C_6H_4$—$C_7H_{14}$—$CH_3$

(10) $H_3C$—$C_9H_{18}$—$C_6H_4$—$OC_2H_4$—$OCO$—$C_2H_4O$—$C_6H_4$—$C_9H_{18}$—$CH_3$

(11) $H_3C$—$C_{17}H_{34}$—$C_6H_4$—$OC_2H_4$—$OCO$—$C_2H_4O$—$C_6H_4$—$C_{17}H_{34}$—$CH_3$

(12) $H_3C$—$C_{19}H_{18}$—$C_6H_4$—$OC_2H_4$—$OCO$—$C_2H_4O$—$C_6H_4$—$C_{19}H_{38}$—$CH_3$

(13) $H_3C$—$\underset{\underset{CH_3}{|}}{\overset{\overset{CH_3}{|}}{C}}$—$C_6H_4$—$OC_2H_4$—$OCO$—$C_2H_4O$—$C_6H_4$—$CH_3$

(14) $H_3C$—$\underset{\underset{CH_3}{|}}{\overset{\overset{CH_3}{|}}{C}}$—$C_6H_4$—$OC_2H_4$—$OCO$—$C_2H_4O$—$C_6H_4$—$C_2H_5$

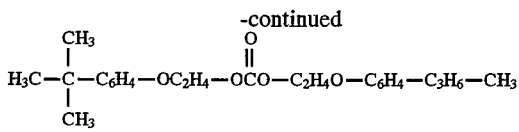

$$H_3C-\underset{\underset{CH_3}{|}}{\overset{\overset{CH_3}{|}}{C}}-C_6H_4-OC_2H_4-O\overset{O}{\overset{||}{C}}O-C_2H_4O-C_6H_4-C_3H_6-CH_3 \quad (15)$$

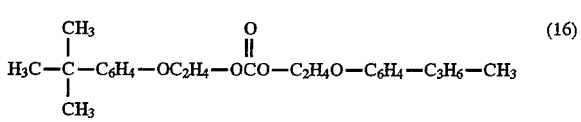

$$H_3C-\underset{\underset{CH_3}{|}}{\overset{\overset{CH_3}{|}}{C}}-C_6H_4-OC_2H_4-O\overset{O}{\overset{||}{C}}O-C_2H_4O-C_6H_4-C_3H_6-CH_3 \quad (16)$$

When the lubricating oil according to the present invention contains the monocarbonate represented by the general formula [I], monocarbonate represented by the general formula [II] and monocarbonate represented by the general formula [III], then the monocarbonate represented by the general formula [I] is used in an amount of from 94 to 5 parts by weight, preferably, from 90 to 10 parts by weight and, more preferably, from 80 to 10 parts by weight, the monocarbonate represented by the general formula [II] is used in an amount of from 92 to 3 parts by weight, preferably, from 85 to 5 parts by weight and, more preferably, from 70 to 10 parts by weight, and the monocarbonate represented by the general formula [III] is used in an amount of from 90 to 3 parts by weight, preferably, from 80 to 5 parts by weight and, more preferably, from 70 to 10 parts by weight per 100 parts by weight of the total of these three kinds of monocarbonates.

Furthermore, the monocarbonate represented by the general formula [I], monocarbonate represented by the general formula [II] and monocarbonate represented by the general formula [III] can be prepared by, for example, a process that is described below.

A mixture of (a) an aromatic ring-containing monoalcohol represented by the general formula [IV]

$$(R^1)_n Ph-O(R^2O)_m H \quad [IV]$$

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands for an aromatic substituent, n stands for an integer of from 1 to 5, and m stands for an integer of from 1 to 30, (b) a monoalcohol represented by the general formula [V]

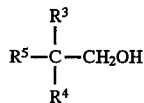

$$R^5-\underset{\underset{R^4}{|}}{\overset{\overset{R^3}{|}}{C}}-CH_2OH \quad [V]$$

wherein $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 20 carbon atoms, and (c) a monocarbonate represented by the general formula [VI]

$$R^6-O\overset{O}{\overset{||}{C}}O-R^7 \quad [VI]$$

wherein $R^6$ and $R^7$, which may be same or different, stand for a hydrocarbon group having 1 to 8 carbon atoms or an etheric oxygen-containing hydrocarbon group having 2 to 8 carbon atoms, is heated in the presence of a basic catalyst, and the formed $R^6OH$ and/or $R^7OH$ and the unreacted monocarbonate represented by the general formula [VI] are distilled off the reaction system to carry out the reaction up to the conversion of not lower than 90%. The conversion of not lower than 90% stands for a reaction that is continued until the $R^6OH$ and/or $R^7OH$ are formed in amounts of not smaller than 0.9 times of mols as great as the number of moles of the aromatic ring-containing monoalcohol (a) represented by the general formula [IV].

In carrying out the reaction, it is desired to substitute the air in the reactor with nitrogen. The air, however, may not be substituted with nitrogen.

Next, the reaction product obtained as described above is washed with water, the basic catalyst is removed followed by dehydration, in order to obtain a desired monocarbonate composition.

Concrete examples of the aromatic ring-containing monoalcohol (a) represented by the general formula [IV], concrete examples of the monoalcohol (b) represented by the general formula [V] and the monocarbonate (c) represented by the general formula [VI] are as described earlier.

Concrete examples of the basic catalyst are the same as the concrete examples of the basic catalyst used for the preparation of the monocarbonate represented by the above-mentioned general formula [I]. The catalyst is used usually in such an amount that the mol number of the catalyst/mol number (mol ratio) of the monoalcohol (b) is from $10^{-1}$ to $10^{-7}$ and, preferably, from $10^{-2}$ to $10^{-5}$.

In this process, the reaction is carried out usually at a temperature of from 50° to 300° C. and, preferably, from 60° to 200° C. The reaction time is usually from 0.5 to 200 hours and, preferably, from 1 to 100 hours.

After the reaction, the catalyst is removed by being washed with water or by being neutralized with acid. Examples of the acid include solid acids such as sulfonic acid type ion-exchange resin and the like; inorganic acids such as carbonic acid, ammonium chloride, hydrochloric acid, sulfuric acid, phosphoric acid and the like; and organic acids such as acetic acid, phenol and the like. In washing the catalyst with water, a salt such as ammonium carbonate may be added.

Prior to removing the catalyst, furthermore, a non-polar solvent may be added, as required, to the carbonate compound that is containing basic substances.

As the non-polar solvent, there can be exemplified aromatic hydrocarbon compounds such as toluene, benzene, xylene and the like, aliphatic hydrocarbon compounds such as hexane, octane and the like, and alicyclic hydrocarbon compounds such as cyclohexane and the like.

According to this process as described above, the above-mentioned desired monocarbonate composition is obtained by distilling off the water or non-polar solvent and trace amounts of unreacted dimethyl carbonates after the basic catalyst has been removed.

The lubricating oil according to the present invention may be blended with other monocarbonates than the monocarbonates represented by the general formulas [II] and [III] in amounts that do not impair the object of the invention.

Examples of such monocarbonates include the following compounds:

$$[CH_3CH_2(CH_3)_2]_2=C_6H_3-OC_2H_4-O\overset{O}{\overset{||}{C}}O-C_2H_4-OCH_3 \quad (1)$$

-continued

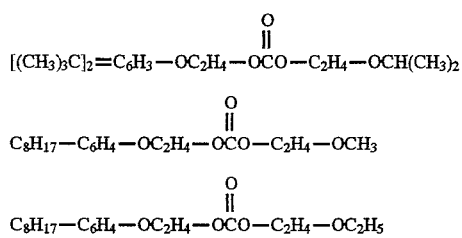

$$C_8H_{17}-C_6H_4-OC_2H_4-OCO-C_2H_4-OCH_3 \quad (3)$$

$$C_8H_{17}-C_6H_4-OC_2H_4-OCO-C_2H_4-OC_2H_5 \quad (4)$$

According to the present invention, the monocarbonate represented by the above-mentioned general formula [II] and the monocarbonate represented by the general formula [III] may be mixed together to prepare a lubricating oil.

When the lubricating oil according to the present invention comprises the monocarbonate represented by the general formula [II] and the monocarbonate represented by the general formula [III], the monocarbonate represented by the general formula [II] is used in an amount of from 95 to 5 parts by weight, preferably from 90 to 10 parts by weight and, more preferably, from 85 to 15 parts by weight and the monocarbonate represented by the general formula [III] is used in an amount of from 90 to 3 parts by weight, preferably from 80 to 10 parts by weight and, more preferably, from 70 to 15 parts by weight per 100 parts by weight of the total of the above two kinds of monocarbonates.

Moreover, the lubricating oil according to the present invention may contain other components than the aforementioned monocarbonate represented by the general formula [I], monocarbonate represented by the general formula [II] and monocarbonate represented by the general formula [III].

When used as an industrial gear oil, as an engine oil for automobiles and as a gear oil for automobiles, the lubricating oil of the present invention may be further blended with mineral oils such as neutral oil, bright stock, etc.

The lubricating oil may be further blended with an α-olefin oligomer such as liquid polybutene, liquid decene oligomer or the like; tetraester of 2-ethylhexanoic acid such as diisooctyl adipate, diisooctyl sebacate, dilauryl sebacate and pentaerythritol; ester of carboxylic acid such as triester of hexanoic acid of trimethylolpropane and the like; plant oil and the like.

When used for the refrigerators, the lubricating oil of the present invention may be further blended with at least one kind of phosphorus compound selected from the group consisting of phosphoric ester, chlorinated phosphoric ester, acid phosphoric ester, amine salt of acid phosphoric ester, tertiary phosphite and secondary phosphite in order to further improve wear resistance and resistance against the load. These phosphorus compounds are esters of phosphoric acid or phosphorous acid and alkanol or polyether-type alcohol, or derivatives thereof.

Concrete examples of phosphoric ester include tributyl phosphate, triphenyl phosphate and tricresyl phosphate.

Concrete examples of chlorinated phosphoric ester include trischloroethyl phosphate, trisdichloropropyl phosphate and the like.

Concrete examples of acid phosphoric ester include ethyl acid phosphate, isopropyl acid phosphate, butyl acid phosphate, 2-ethylhexyl acid phosphate, lauryl acid phosphate, tetradecyl acid phosphate, pentadecyl acid phosphate, hexadecyl acid phosphate, heptadecyl acid phosphate, octadecyl acid phosphate, stearyl acid phosphate, isostearyl acid phosphate and oleyl acid phosphate.

Concrete examples of amine salt of acid phosphoric ester include octylamine, oleylamine, coconutamine and beef tallowamine of the acid phosphoric ester.

Concrete examples of tertiary phosphite include triphenyl phosphite, tricresyl phosphite, diphenylisodecyl phosphite, phenyldiisodecyl phosphite, tristearyl phosphite and trilauryl phosphite.

Concrete examples of the secondary phosphite include di-2-ethylhexylhydrodiene phosphite, dilaurylhydrodiene phosphite and dioleylhydrogen phosphite.

These phosphorus compounds can be used alone or in a combination.

It is desired that these phosphorus compounds are blended in an amount of from 0.0005 to 10.0% by weight and, preferably, from 0.001 to 5.0% by weight per the whole amount of the lubricating oil.

According to the present invention, furthermore, it is allowable to add to the lubricating oil widely known additives such as cleaning/dispersing agent, anti-oxidizing agent, load resistance improver, oil agent, and fluidizing point dropper that have been disclosed in Toshio Sakurai, "Petroleum Product Additives" (Saiwai Shobo Co., 1974) in amounts that do not impair the object of the invention. In the case of the lubricating oil for refrigerators that use HFC such as R-134a, R-125 or R-32 as an ozone layer non-depleting coolant gas, the components that can be added are limited to be acetals, glycol ethers and carboxylic esters from the standpoint of compatibility. These components, however, deteriorates heat resistance, compatibility to R-134a and hygroscopic property. Therefore, these components must be added in amounts of less than 60% by weight per 100% by weight of the whole amount of the lubricating oil.

The lubricating oil of the present invention may be further blended with an epoxy compound, a phenol-type stabilizer or a defoaming agent as a chlorine-trapping agent to cope with the infiltration of the chlorine-containing coolant. The lubricating oil for refrigerators may further contain hydrogenated fluorocarbon such as R-134a, hydrogenated chlorofluorocarbon such as R-22 or a mixture thereof.

When the lubricating oil of the present invention is used for rolling, for machining metals and for fibers, furthermore, the monocarbonate represented by the general formula [I], [II] or [III] may be used in the form of an emulsion with water by using a suitable emulsifying agent.

The monocarbonate according to the present invention is of the type that is substituted with many alkyl groups, and has a carbonic acid bond that is protected.

The lubricating oil of the present invention contains the monocarbonate of the type substituted with many alkyl groups, and exhibits excellent lubricating property, cleaning property and electrically insulating property. Besides, the lubricating oil of the invention is not decomposed and does not form carboxylic acid unlike the carboxylic ester-type lubricating oils. Compared with the conventional polycarbonate-type lubricating oils, furthermore, the lubricating oil of the invention suppresses the evolution of carbonic acid gas that stems from the decomposition of the carbonate compounds.

Therefore, the lubricating oil of the present invention can be extensively used as lubricating oil for refrigerators of car air conditioners, electric refrigerators, air conditioners for room, as industrial gear oil, as engine oil for automobiles, as gear oil for automobiles, as lubricating oil for fibers, as lubricating oil for rolling and as traction oil.

Moreover, the lubricating oil of the present invention exhibits not only the above-mentioned excellent properties but also excellent compatibility with hydrogenated fluorocarbons such as R-134a, excellent compatibility with hydrogenated chlorofluorocarbons such as R-22 and excellent compatibility with mixtures thereof. Accordingly, the lubricating oil of the invention can be favorably used for the refrigerators such as electric refrigerators and air conditioners for room that use the above-mentioned hydrogenated compounds as coolants.

EXAMPLES

The present invention will now be described by way of examples to which only, however, the invention is in no way limited.

In Examples and Comparative Examples, analysis of carbonates and evaluation of performance of the lubricating oils were conducted in compliance with the following testing methods.

(1) Chemical formula of carbonate compound.

IR analysis, protonic NMR analysis (2) Method of evaluation.

a. Dynamic viscosity. JIS K-2283 b. Resistance against the load.

By using a Falex testing machine, the running-in is carried out for five minutes under the load of 250 lbf. The load is then increased and a value is found at which seizure takes place. The value at this moment is regarded to be resistance against the load.

c. Method of measuring the carbonic acid gas concentration.

An autoclave having a volume of 50 cc with which the sampling port of a gas chromatography is equipped in the upper portion, is filled with 25 g of a sample oil and is hermetically sealed in a nitrogen atmosphere.

The autoclave is then heated by using a constant-temperature oil bath heated at 200° C. Seven hours after the start of the heating, 1 cc of a gas inside the autoclave is picked up using a gas syringe through the gas-sampling port. The $CO_2$ concentration produced by the sampling oil is measured using the gas chromatography.

Column: AC 6M

Column temperature: 165° C.

Kind of carrier gas and feeding rate: He, 40 ml/min.

Detector: TCD (heat conductivity detector)

d. Compatibility with the mixture of hydrogenated fluorocarbons (mixture gas of R-134a/R-32/R-125=60/30/10).

(1) One milliliter of a sample is introduced into a test tube having an inner diameter of 10 mm and a depth of 20 cm, and the mixture of the hydrogenated fluorocarbons is slowly introduced from a container into the test tube while it is being cooled in a dry ice-acetone bath until its amount is larger than that of the sample. Then, these liquids are stirred using a spatula. The mixture is transferred into a coolant bath of −10° C., and dissolving property is checked when the volume ratio of sample/mixture of hydrogenated fluorocarbons is 1/1. A completely homogeneous state is represented by ○ and a state in which they are not dissolved is represented by X.

(2) In order to more closely examine the compatibility between the carbonate product and the mixture of hydrogenated fluorocarbons, the lubricating oil and the mixture of hydrogenated fluorocarbon are introduced into a glass tube by changing their ratio, in order to find a limit temperature (critical temperature) at which the two become compatible with each other.

Comparative Example 1

A mixture of 250 g of a polypropylene glycol monobutyl ether having an average molecular weight of 86, 999 g of 30 times mol ratio excess of a diethyl carbonate, and 1.0 g of a methanol solution containing 8% by weight of $NaOCH_3$ (catalyst), was heated at 80° to 20° C. and was reacted while distilling off the formed ethanol, to obtain 260 g of a monocarbonate represented by the following chemical formula,

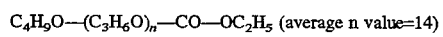

$C_4H_9O$—$(C_3H_6O)_n$—$CO$—$OC_2H_5$ (average n value=14)

Table 1 shows the evaluation of basic performance of the lubricating oil of the obtained monocarbonate.

The lubricating oil for the electric refrigerators and the air conditioners for room must have an electrically insulating property, i.e., a volume resistivity, of not smaller than $10^{12}\Omega\cdot cm$ and, preferably, not smaller than $10^{13}\Omega\cdot cm$. As will be obvious from Table 1, however, the monocarbonate obtained in Comparative Example 1 has a volume resistivity of as low as $2\times10^{11}\Omega\cdot cm$ and is not suited for use as a lubricating oil for the electric refrigerators and air conditioners for room.

Comparative Example 2

A mixture of 250 g of an adduct of a paraisooctylphenol having an average molecular weight of 250 to which has been added 1 mol of an ethylene oxide, 900 g of 10 times mol ratio excess of a diethyl carbonate, and 1.0 g of a methanol solution containing 28% by weight of $NaOCH_3$ (catalyst), was heated at 70° to 90° C. and was reacted while distilling off the formed methanol, to obtain 255 g of a monocarbonate represented by the following chemical formula,

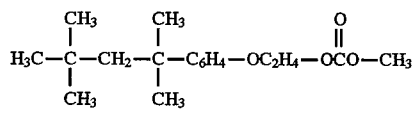

Table 1 shows the evaluation of basic performance of the obtained monocarbonate lubricating oil.

Comparative Examples 3 to 8

Carbonates represented by the following formulae were obtained by using the preparation method analogous to the above-mentioned the Comparative Examples.

Carbonate of Comparative Example 3

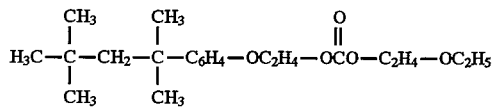

Carbonate of Comparative Example 4

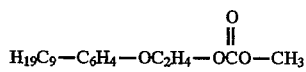

Carbonate of Comparative Example 5

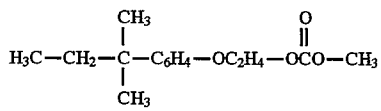

Carbonate of Comparative Example 6

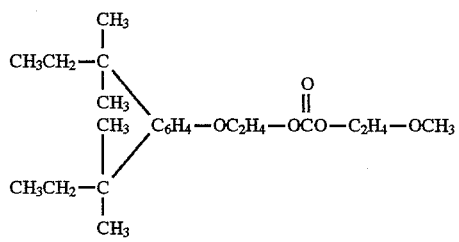

Carbonate of Comparative Example 7

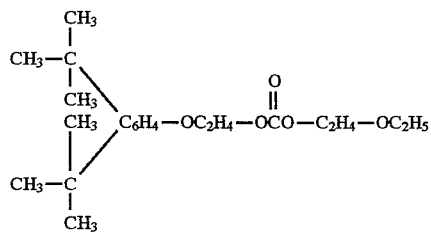

Carbonate of Comparative Example 8

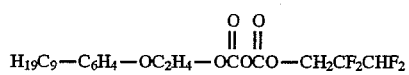

Table 1 shows evaluation results of a basic lubricating oil property of the above-mentioned each monocarbonate.

Reference Example 1

Into a flask having a capacity of 5 liters were fed 1510 g of a neopentyl glycol, 2200 g of a dioxane and 100 g of a catalyst (Amberlist 15 produced by Organo Co.), and the reaction was carried out for 5 hours while feeding isobutene thereto at room temperature.

After the reaction, the catalyst was removed, followed by isolation by distillation to obtain 1200 g of a neopentyl glycol mono-t-butyl ether.

Then, into a flask having a capacity of 3 liters equipped with a 10-stage sieve tray-type distilling device were fed 1171 g (7.3 mols) of the neopentyl glycol mono-t-butyl ether, 658 g (7.3 mols) of a dimethyl carbonate and 3.1 g (0.02 mols) of a methanol solution containing 28% by weight of $NaOCH_3$.

The mixture was then heated under normal pressure at 100° to 170° C. for 5 hours, and was further heated under a reduced pressure of 700 to 11 mmHg at 170° C. for 4 hours to distill off the formed methyl alcohol and unreacted dimethyl carbonate. Distillation was further continued under a reduced pressure of 10 mmHg at 180° C., to obtain 1180 g of a monocarbonate (hindered monocarbonate) having the following structure that could be little decomposed.

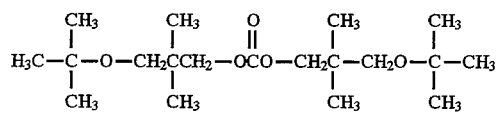

Table 1 shows the evaluation of basic performance of the obtained monocarbonate lubricating oil.

Reference Example 2

Into a flask having a capacity of 5 liters were fed 1500 g of a 2-ethyl-2-butyl-1,3-propanediol, 2200 g of a dioxane and 100 g of a catalyst (Amberlist 15 produced by Organo Co.), and the reaction was carried out for 5 hours while feeding isobutene thereto at room temperature.

After the reaction, the catalyst was removed, followed by isolation by distillation to obtain 1305 g of a 2-ethyl-2-butyl-1,3-propanediol mono-t-butyl ether.

Then, into a flask having a capacity of 2 liters equipped with a 10-stage sieve tray-type distilling device were fed 946 g (4.4 mols) of the 2-ethyl-2-butyl-1,3-propanediol mono-t-butyl ether, 390 g (4.3 mols) of a dimethyl carbonate and 1.5 g (0.008 mols) of a methanol solution containing 28% by weight of $NaOCH_3$.

The mixture was then heated under a reduced pressure of 300 to 10 mmHg at 180° to 190° C. for 5 hours to distill off the formed methyl alcohol and unreacted dimethyl carbonate. Distillation was further continued under a reduced pressure of 5 mmHg at 190° C., to obtain 908 g of a monocarbonate (hindered monocarbonate) having the following structure.

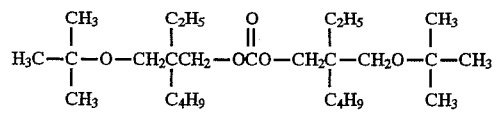

Table 1 shows the evaluation of basic performance of the obtained monocarbonate lubricating oil.

Reference Example 3

Into a flask having a capacity of 3 liters equipped with a 10-stage sieve tray-type distilling device were fed 703 g of an adduct of a para-t-butylphenol to which has been added 1 mole of an ethylene oxide, 666 g of a dimethyl carbonate and 1.3 g of a methanol solution containing 28% by weight of $NaOCH_3$.

The mixture was then heated under normal pressure at 90° to 170° C. for 5 hours, and was further heated under a reduced pressure of 700 to 11 mmHg at 170° C. for 4 hours to distill off the formed methyl alcohol and unreacted dimethyl carbonate, in order to obtain 726 g of a monocarbonate having the following structure.

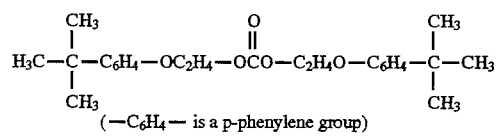

( —$C_6H_4$— is a p-phenylene group)

Table 1 shows the evaluation of basic performance of the obtained monocarbonate lubricating oil.

EXAMPLE 1

To a flask having a capacity of 5 liters were fed 721 g of an adduct of a para-t-butylphenol to which has been added 1 mole of an ethylene glycol, 3868 g of the hindered monocarbonate synthesized in Reference Example 1, and 3.6 g of a methanol solution containing 28% by weight of $NaOCH_3$.

The mixture was then heated under a reduced pressure of 3 mmHg at 160° to 190° C. for 5 hours to distill off the formed neopentyl glycol mono-t-butyl ether. The conversion was 98%. The thus obtained reaction mixture was washed with water, and the catalyst was removed therefrom. Then, an excess of the hindered monocarbonate synthesized in Reference Example 1 was distilled off, and 927 g of a monocarbonate of the following structure was obtained by distillation.

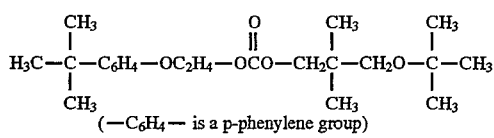
(—C$_6$H$_4$— is a p-phenylene group)

IR and 1H-NMR absorption characteristic spectrum of the above monocarbonate are as follows;

$^1$H-NMR (CDCl$_3$)
0.9 ppm
1.3
3.8–4.2
6.8–7.5

IR
| ν C—H | 2800–3100 cm$^{-1}$ |
| δ C—H | 1350–1510 |
| ν C=O | 1740 |
| ν C—O | 1180–1300 |
| ν C—O—C | 1080 |

Table 1 shows the evaluation of basic performance of the obtained monocarbonate lubricating oil.

EXAMPLE 2

To a flask having a capacity of 3 liters were fed 208 g of an adduct of a para-t-amylphenol to which has been added 1 mole of an ethylene glycol, 2003 g of the hindered monocarbonate synthesized in Reference Example 1, and 3.2 g of a methanol solution containing 28% by weight of NaOCH$_3$.

The mixture was then heated under a reduced pressure of 3 mmHg at 160° to 190° C. for 5 hours to distill off the formed neopentyl glycol mono-t-butyl ether. The conversion was 98%. The thus obtained reaction mixture was washed with water, and the catalyst was removed therefrom. Then, an excess of the hindered monocarbonate synthesized in Reference Example 1 was distilled off, and 340 g of a monocarbonate of the following structure was obtained by distillation.

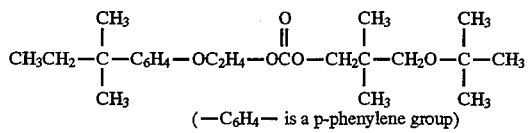
(—C$_6$H$_4$— is a p-phenylene group)

IR and $^1$H-NMR absorption characteristic spectrum of the above monocarbonate are as follows;

$^1$H-NMR (CDCl$_3$)
0.9 ppm
1.3
1.5–2.0
3.8–4.2
6.8–7.5

IR
| ν C—H | 2800–3100 cm$^{-1}$ |
| δ C—H | 1350–1520 |
| ν C=O | 1740 |
| ν C—O | 1180–1300 |
| ν C—O—C | 1080 |

Table 1 shows the evaluation of basic performance of the obtained monocarbonate lubricating oil.

EXAMPLE 3

To a flask having a capacity of 3 liters were fed 354 g of an adduct of a para-sec-butylphenol to which has been added 1 mole of an ethylene glycol, 2518 g of the hindered monocarbonate synthesized in Reference Example 1, and 1.8 g of a methanol solution containing 28% by weight of NaOCH$_3$.

The mixture was then heated under a reduced pressure of 3 mmHg at 140° to 190° C. for 4 hours to distill off the formed neopentyl glycol mono-t-butyl ether. The conversion was 99%. The thus obtained reaction mixture was washed with water, and the catalyst was removed therefrom. Then, an excess of the hindered monocarbonate synthesized in Reference Example 1 was distilled off, and 537 g of a monocarbonate of the following structure was obtained by distillation.

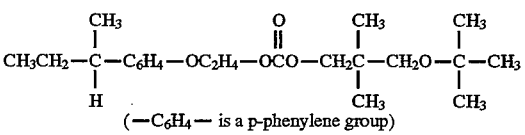
(—C$_6$H$_4$— is a p-phenylene group)

IR and $^1$H-NMR absorption characteristic spectrum of the above monocarbonate are as follows;

$^1$H-NMR (CDCl$_3$)
0.9 ppm
1.3
1.5–2.0
3.8–4.2
6.8–7.5

IR
| ν C—H | 2800–3100 cm$^{-1}$ |
| δ C—H | 1350–1520 |
| ν C=O | 1740 |
| ν C—O | 1180–1300 |
| ν C—O—C | 1080 |

Table 1 shows the evaluation of basic performance of the obtained monocarbonate lubricating oil.

EXAMPLE 4

To a flask having a capacity of 3 liters were fed 180 g of an adduct of a metaisopropylphenol to which has been added 1 mole of an ethylene glycol, 1734 g of the hindered monocarbonate synthesized in Reference Example 1, and 2.2 g of a methanol solution containing 28% by weight of NaOCH$_3$.

The mixture was then heated under a reduced pressure of 30 to 5 mmHg at 140° to 190° C. for 4 hours to distill off the formed neopentyl glycol mono-t-butyl ether. The conversion was 99%. The thus obtained reaction mixture was washed with water, and the catalyst was removed therefrom. Then, an excess of the hindered monocarbonate synthesized in Reference Example 1 was distilled off, and 223 g of a monocarbonate of the following structure was obtained by distillation.

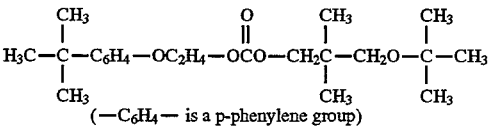
(—C$_6$H$_4$— is a p-phenylene group)

IR and $^1$H-NMR absorption characteristic spectrum of the dove monocarbonate are as follows;

¹H-NMR (CDCl₃)
0.9 ppm
1.3
1.5–2.0
3.8–4.2
6.8–7.5

IR
| | |
|---|---|
| ν C—H | 2800–3100 cm⁻¹ |
| δ C—H | 1350–1520 |
| ν C=O | 1740 |
| ν C—O | 1180–1300 |
| ν C—O—C | 1080 |

Table 1 shows the evaluation of basic performance of the obtained monocarbonate lubricating oil.

EXAMPLE 5

110 Grams of the monocarbonate synthesized in Example 1 and 90 g of the monocarbonate synthesized in Example 4 were blended together to obtain the following monocarbonate composition.

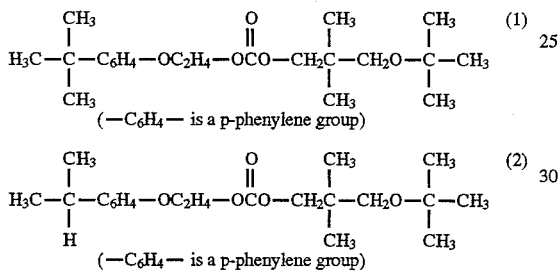

Table 1 shows the evaluation of basic performance of the obtained monocarbonate composition lubricating oil.

EXAMPLE 6

To a flask having a capacity of 2 liters equipped with a single distillating device were fed 400 g (2.06 mols) of an adduct of a para-t-butylphenol to which has been added 1 mole of an ethylene oxide, 857 g (2.48 mols) of the hindered monocarbonate synthesized in Reference Example 1, and 1.0 g (0.005 mols) of a methanol solution containing 28% by weight of NaOCH₃.

The mixture was then heated under a reduced pressure of 30 to 3 mmHg at 140° to 175° C. for 2.5 hours, and the formed neopentyl glycol mono-t-butyl ether was distilled off. The conversion was 98%.

The thus obtained reaction mixture was washed with water and the catalyst was removed therefrom. The reaction mixture was then dehydrated to obtain 810 g of the following monocarbonate composition.

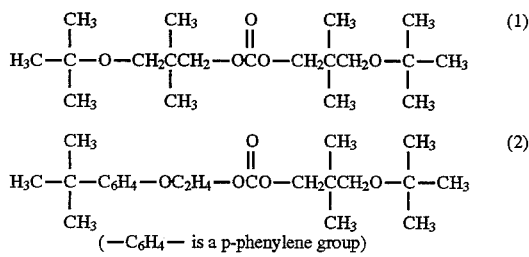

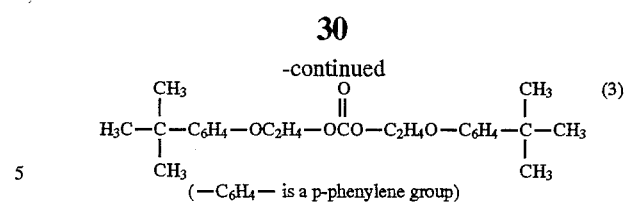

(1)/(2)/(3)=23.5/51.0/22.9 (% by weight)

Table 1 shows the evaluation of basic performance of the obtained monocarbonate composition lubricating oil.

EXAMPLE 7

267 Grams of the monocarbonate synthesized in Reference Example 1, 493 g of the monocarbonate synthesized in Example 1 and 184 g of the monocarbonate synthesized in Reference Example 3 were blended together to obtain the following monocarbonate composition.

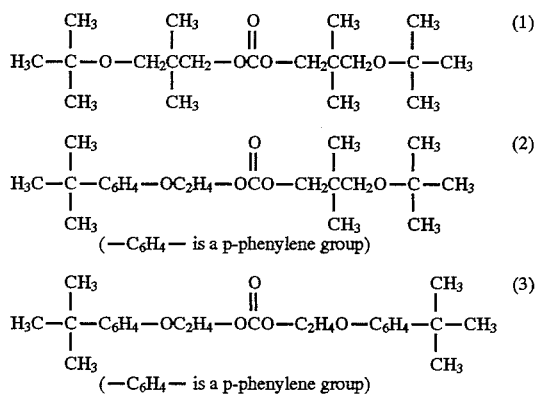

(1)/(2)/(3)=24.8/49.8/20.2 (% by weight)

Table 1 shows the evaluation of basic performance of the obtained monocarbonate composition lubricating oil.

EXAMPLE 8

Into a flask having a capacity of 3 liters equipped with a 10-stage sieve tray-type distilling device were fed 489 g of an adduct of a para-t-butylphenol to which has been added 1 mole of an ethylene oxide, 565 g of a neopentyl glycol mono-t-butyl ether, 823 g of a dimethyl carbonate and 2.8 g of a methanol solution containing 28% by weight of NaOCH₃.

The mixture was then heated under normal pressure at 90° to 180° C. for 5 hours to distill off the formed methyl alcohol and unreacted dimethyl carbonate. The mixture was further heated under a reduced pressure of 300 to 3 mmHg at 170° C. for 4 hours in order to distill off the formed monocarbonate that was an intermediate product.

The thus obtained reaction mixture was washed with water and the catalyst was removed therefrom. The reaction mixture was then dehydrated in order to obtain 996 g of the following monocarbonate composition.

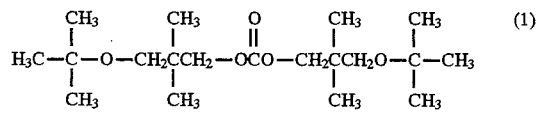

-continued

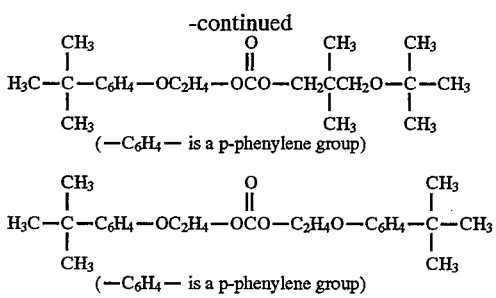

(1)/(2)/(3)=22.5/50.4/20.6 (% by weight)

Table 1 shows the evaluation of basic performance of the obtained monocarbonate composition lubricating oil.

EXAMPLE 9

Into a flask having a capacity of 5 liters equipped with a single distilling device were fed 995 g (5.12 mols) of an adduct of a para-t-butylphenol to which has been added 1 mole of an ethylene oxide, 3621 g (10.54 mols) of the hindered monocarbonate synthesized in Reference Example 1, and 5.3 g (0.005 mols) of a methanol solution containing 28% by weight of NaOCH$_3$.

The mixture was then heated under a reduced pressure of 30 to 3 mmHg at 140° to 175° C. for 2.5 hours to distill off the formed neopentyl glycol mono-t-butyl ether. The conversion was 98%.

The thus obtained reaction mixture was washed with water and the catalyst was removed therefrom. The reaction mixture was further dehydrated, and 1990 g of the unreacted hindered monocarbonate was distilled off in order to obtain 1780 g of the following monocarbonate composition.

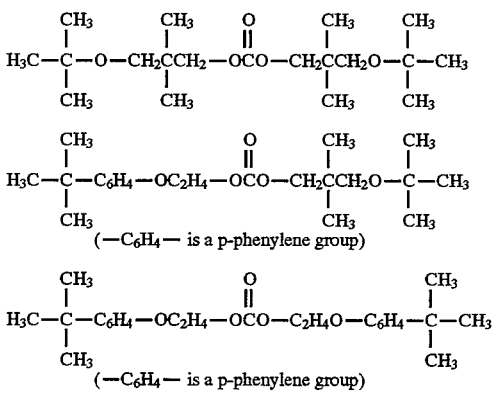

(1)/(2)/(3)=15.3/72.0/12.1 (% by weight)

Table 1 shows the evaluation of basic performance of the obtained monocarbonate composition lubricating oil.

EXAMPLE 10

13 Grams of the monocarbonate synthesized in Reference Example 1 and 238 g of the monocarbonate synthesized in Example 1 were blended together to obtain the following monocarbonate composition.

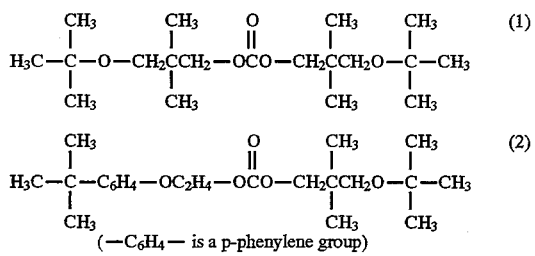

(1)/(2)=7.2/91.4 (% by weight)

Table 1 shows the evaluation of basic performance of the obtained monocarbonate composition lubricating oil.

EXAMPLE 11

Into a flask having a capacity of 3 liters equipped with a single distilling device were fed 396 g (2.04 mols) of an adduct of a para-t-butylphenol to which has been added 1 mole of an ethylene oxide, 1296 g (3.75 mols) of the hindered monocarbonate synthesized in Reference Example 1, and 1.0 g (0.005 mols) of a methanol solution containing 28% by weight of NaOCH$_3$.

The mixture was then heated under a reduced pressure of 30 to 3 mmHg at 140° to 175° C. for 2.5 hours to distill off the formed neopentyl glycol mono-t-butyl ether. The conversion was 99%.

The thus obtained reaction mixture was washed with water and the catalyst was removed therefrom. The reaction mixture was further dehydrated in order to obtain 1309 g of the following monocarbonate composition.

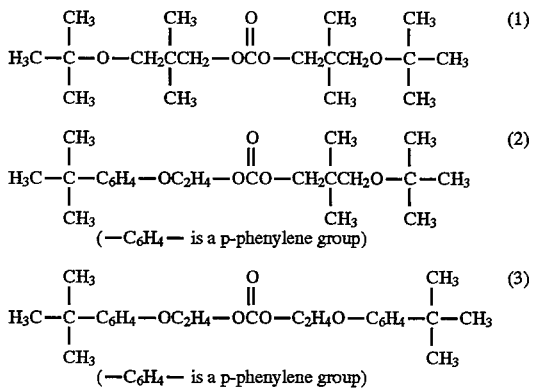

(1)/(2)/(3)=43.1/44.4/11.1 (% by weight)

Table 1 shows the evaluation of basic performance of the obtained monocarbonate composition lubricating oil.

EXAMPLE 12

Into a flask having a capacity of 3 liters equipped with a 10-stage sieve tray-type distilling device were fed 300 g of an adduct of a para-t-butylphenol to which has been added 1 mole of an ethylene oxide, 565 g of a neopentyl glycol mono-t-butyl ether, 584 g of a dimethyl carbonate and 2.1 g of a methanol solution containing 28% by weight of NaOCH$_3$.

The mixture was then heated under normal pressure at 90° to 180° C. for 5 hours to distill off the formed methyl alcohol and unreacted dimethyl carbonate; and was further heated under a reduced pressure of 300 to 3 mmHg at 170° C. for 4 hours to distill off part of the formed monocarbonate that was an intermediate product.

The thus obtained reaction mixture was washed with water and the catalyst was removed therefrom. The reaction mixture was further dehydrated to obtain 948 g of the following monocarbonate composition.

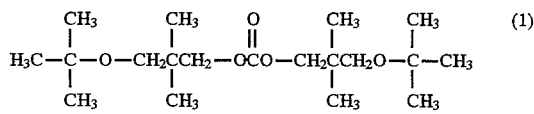

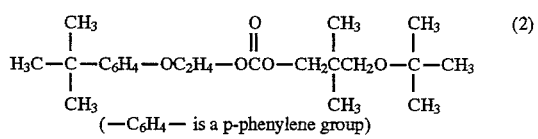

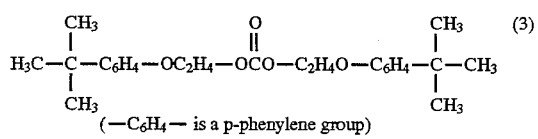

(1)/(2)/(3)=44.5/44.8/8.7 (% by weight)

Table 2 shows the evaluation of basic performance of the obtained monocarbonate composition lubricating oil.

EXAMPLE 13

Into a flask having a capacity of 5 liters were fed 208 g of an adduct of a para-t-amylphenol to which has been added 1 mole of an ethylene glycol, 731 g of the hindered monocarbonate synthesized in Reference Example 1, and 2.2 g of a methanol solution containing by weight of $NaOCH_3$.

The mixture was then heated under a reduced pressure of 3 mmHg at 160° to 190° C. for 5 hours to distill off the formed neopentyl glycol mono-t-butyl ether in order to obtain 284 g of a monocarbonate having the following structure (2).

Next, this monocarbonate was blended with 62 g of the monocarbonate synthesized in Reference Example 1 in order to obtain 346 g of the following monocarbonate composition.

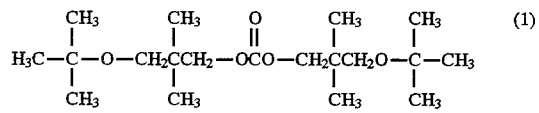

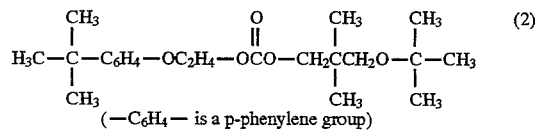

(1)/(2)=18/82 (% by weight)

Table 2 shows the evaluation of basic performance of the obtained monocarbonate composition lubricating oil.

EXAMPLE 14

Into a flask having a capacity of one liter equipped with a single distilling device were fed 102 g (0.49 mols) of an adduct of a para-t-amylphenol to which has been added 1 mole of an ethylene oxide, 306 g (0.94 mols) of the hindered monocarbonate synthesized in Reference Example 1, and 0.4 g (0.002 mols) of a methanol solution containing 28% by weight of $NaOCH_3$.

The mixture was then heated under a reduced pressure of 30 to 3 mmHg at 140° to 175° C. for 2.5 hours to distill off the formed neopentyl glycol mono-t-butyl ether. The conversion was 99%.

The thus obtained reaction mixture was washed with water and the catalyst was removed therefrom. The reaction mixture was further dehydrated in order to obtain 1368 g of the following monocarbonate composition.

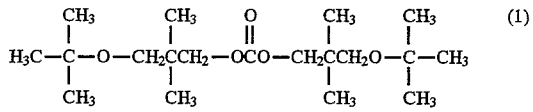

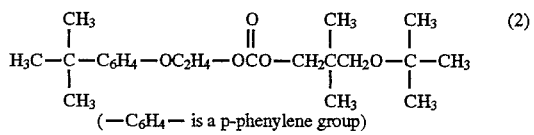

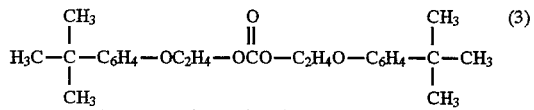

(1)/(2)/(3)=38.2/45.9/7.8 (% by weight)

Table 2 shows the evaluation of basic performance of the obtained monocarbonate composition lubricating oil.

EXAMPLE 15

Into a flask having a capacity of 3 liters equipped with a single distilling device were fed 355 g of an adduct of a para-t-amylphenol to which has been added 1 mole of an ethylene oxide, 1600 g of a di(methoxy-ethyl) carbonate, and 2.4 g of a methanol solution containing 28% by weight of $NaOCH_3$.

The mixture was then heated under a reduced pressure of 60 to 30 mmHg at 100° to 145° C. for 2.0 hours to distill off the formed ethylene glycol monomethyl ether. The conversion was 99%.

The thus obtained reaction mixture was washed with water and the catalyst was removed therefrom. The reaction mixture was further dehydrated to obtain 390 g of the following monocarbonate (2). 227 Grams of this monocarbonate was blended with 65 g of the hindered monocarbonate synthesized in Reference Example 1 in order to obtain the following monocarbonate composition.

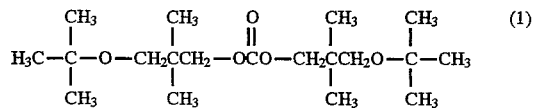

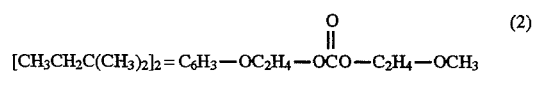
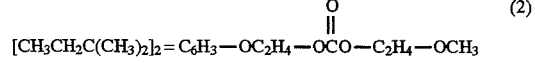

(1)/(2)/=32.3/67.7 (% by weight)

Table 2 shows the evaluation of basic performance of the obtained monocarbonate composition lubricating oil.

EXAMPLE 16

44 Grams of the monocarbonate synthesized in Reference Example 1 and 156 g of the monocarbonate synthesized in Example 4 were blended together to obtain the following monocarbonate composition.

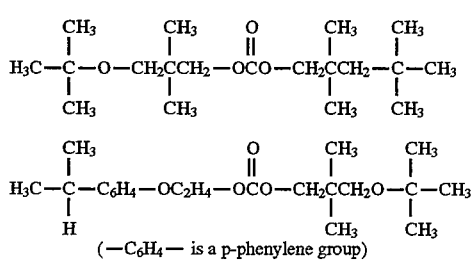

(—C₆H₄— is a p-phenylene group)

(1)/(2)=22/78 (% by weight)

Table 2 shows the evaluation of basic performance of the obtained monocarbonate composition lubricating oil.

EXAMPLE 17

80 Grams of the monocarbonate synthesized in Reference Example 2 and 120 g of the monocarbonate synthesized in Example 4 were blended together to obtain the following monocarbonate composition.

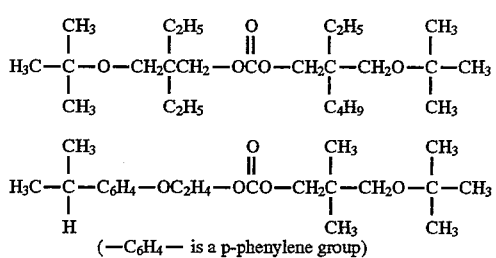

(—C₆H₄— is a p-phenylene group)

(1)/(2)=40/60 (% by weight)

Table 2 shows the evaluation of basic performance of the obtained monocarbonate composition lubricating oil.

In Examples 1 to 17 mentioned above, $CO_2$ is generated in small amounts, heat stability is improved, good Falex lubricating property is exhibited and excellent balance is maintained between the heat stability and the lubricating property compared with those of Comparative Examples 1 and 2.

EXAMPLE 18

The monocarbonate composition synthesized in Example 8 was blended with 1% by weight of a tricresyl phosphate (TCP).

Table 2 shows the evaluation of basic performance of the thus obtained lubricating oil.

EXAMPLE 19

The monocarbonate composition synthesized in Example 8 was blended with 1% by weight of a triphenyl phosphate (TPP).

Table 2 shows the evaluation of basic performance of the thus obtained lubricating oil.

EXAMPLE 20

The monocarbonate composition synthesized in Example 12 was blended with 1% by weight of a triphenyl phosphate (TPP).

Table 2 shows the evaluation of basic performance of the thus obtained lubricating oil.

In Examples 18 to 20, it was recognized that phosphorus compounds that were blended helped improve lubricating property and heat stability.

TABLE 1

| | Dynamic viscosity at 40° C. [cSt] | Electric insulation, volume resistivity [Ω · cm] | Load resistance [lbf] | Compatibility with mixed HFC | | | Evolution of $CO_2$ [Vol %] |
|---|---|---|---|---|---|---|---|
| | | | | (1) note 1) | (2) (°C.) note 2) | | |
| | | | | | Hi temp. side | Lo temp. side | |
| Comp. Ex. 1 | 42.5 | $2 \times 10^{11}$ | 860 | O | >47 | −55 | 4.8 |
| Comp. Ex. 2 | 58.9 | $4 \times 10^{13}$ | 900 | O | >80 | −31 | 2.4 |
| Comp. Ex. 3 | 66.9 | $3 \times 10^{13}$ | 980 | O | >80 | −20 | 2.4 |
| Comp. Ex. 4 | 52.3 | $3 \times 10^{13}$ | 920 | O | 45 | 25 | 2.2 |
| Comp. Ex. 5 | 20.4 | $1 \times 10^{13}$ | 910 | O | >80 | −58 | 2.4 |
| Comp. Ex. 6 | 62.7 | $4 \times 10^{13}$ | 970 | O | 80 | −39 | 2.2 |
| Comp. Ex. 7 | 59.0 | $5 \times 10^{13}$ | 960 | O | >80 | −55 | 2.3 |
| Comp. Ex. 8 | 109.8 | $3 \times 10^{12}$ | 980 | O | 80 | −28 | 2.2 |
| Ref. Ex. 1 | 12.0 | $1 \times 10^{13}$ | 800 | O | >80 | <−65 | 0.8 |
| Ref. Ex. 2 | 79.0 | $4 \times 10^{13}$ | 950 | O | >80 | 0 | 0.5 |
| Ref. Ex. 3 | 393.1 | $1 \times 10^{13}$ | 1120 | X | — | — | 2.1 |
| Ex. 1 | 77.9 | $2 \times 10^{14}$ | 980 | O | 75 | −27 | 1.4 |
| Ex. 2 | 81.8 | $1 \times 10^{14}$ | 990 | O | 65 | −15 | 1.3 |
| Ex. 3 | 48.7 | $8 \times 10^{13}$ | 970 | O | 73 | −4 | 1.5 |
| Ex. 4 | 45.4 | $5 \times 10^{13}$ | 950 | O | >80 | −26 | 1.6 |
| Ex. 5 | 64.4 | $6 \times 10^{13}$ | 960 | O | >80 | −22 | 1.5 |
| Ex. 6 | 68.8 | $4 \times 10^{13}$ | 980 | O | 72 | −10 | 0.9 |
| Ex. 7 | 67.3 | $3 \times 10^{13}$ | 980 | O | 75 | −12 | 0.9 |
| Ex. 8 | 66.8 | $4 \times 10^{13}$ | 980 | O | 75 | −12 | 0.9 |
| Ex. 9 | 66.2 | $3 \times 10^{13}$ | 990 | O | 77 | −21 | 1.0 |
| Ex. 10 | 68.2 | $1 \times 10^{14}$ | 970 | O | 78 | −27 | 1.1 | note 1) O: compatible X: not compatible
note 2) Compatible range with mixed HFC (mixture of hydrogenated fluorocarbons of R-134a/R-32/R-125 = 60/30/10%).

TABLE 2

| | Dynamic viscosity at 40° C. [cSt] | Electric insulation, volume resistivity [Ω · cm] | Load resistance [lbf] | Compatibility with mixed HFC | | | Evolution of $CO_2$ [Vol %] |
|---|---|---|---|---|---|---|---|
| | | | | (1) note 1) | (2) (°C.) note 2) | | |
| | | | | | Hi temp. side | Lo temp. side | |
| Ex. 11 | 32.4 | $2 \times 10^{13}$ | 960 | ○ | >80 | −50 | 0.9 |
| Ex. 12 | 33.9 | $2 \times 10^{13}$ | 960 | ○ | >80 | −50 | 0.9 |
| Ex. 13 | 65.3 | $9 \times 10^{13}$ | 990 | ○ | 75 | −10 | 1.0 |
| Ex. 14 | 36.0 | $2 \times 10^{13}$ | 970 | ○ | 78 | −23 | 0.9 |
| Ex. 15 | 35.0 | $3 \times 10^{13}$ | 980 | ○ | >80 | −55 | 1.1 |
| Ex. 16 | 32.1 | $2 \times 10^{13}$ | 970 | ○ | >80 | −35 | 0.9 |
| Ex. 17 | 56.2 | $4 \times 10^{13}$ | 990 | ○ | >80 | −15 | 0.8 |
| Ex. 18 | 66.7 | $3 \times 10^{13}$ | 1220 | ○ | 75 | −12 | 0.04 |
| Ex. 19 | 66.7 | $3 \times 10^{13}$ | 1200 | ○ | 75 | −12 | 0.04 |
| Ex. 20 | 33.4 | $2 \times 10^{13}$ | 1180 | ○ | >80 | −50 | 0.04 | note 1) ○: compatible X: not compatible
note 2) Compatible range with mixed HFC (mixture of hydrogenated fluorocarbons of R-134a/R-32/R-125 = 60/30/10%).

What is claimed is:

1. A monocarbonate represented by the following general formula [I];

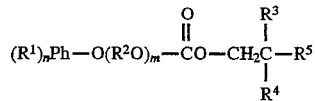

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 20 carbon atoms, Ph stands for an aromatic substituent, n stands for an integer of from 1 to 5, and m stands for an integer of from 1 to 30.

2. A lubricating oil containing a monocarbonate represented by the following general formula [I];

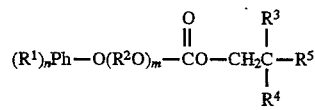

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, $R^3$, $R^4$ and $R^5$, which may be same or different, stand for a hydrocarbon group having 1 to 20 carbon atoms, an alkoxy group having 1 to 12 carbon atoms or an etheric oxygen-containing hydrocarbon group having 2 to 20 carbon atoms, Ph stands for an aromatic substituent, n stands for an integer of from 1 to 5, and m stands for an integer of from 1 to 30.

3. A lubricating oil according to claim 2, wherein said lubricating oil contains, in addition to the monocarbonate represented by the general formula [I], a monocarbonate represented by the following general formula [II];

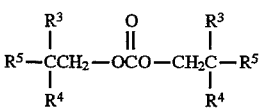

wherein $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 20 carbon atoms.

4. A lubricating oil according to claim 3, wherein said lubricating oil contains, in addition to the monocarbonates represented by the general formulas [I] and [II], a monocarbonate represented by the following general formula [III];

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands each independently for an aromatic substituent, n stands each independently for an integer of from 1 to 5, and m stands each independently for an integer of from 1 to 30.

5. A lubricating oil according to any one of claim 2 to claim 4, wherein said lubricating oil is used for refrigerators.

6. A lubricating oil for refrigerator use according to claim 5, wherein said lubricating oil further contains a hydrogenated fluorocarbon.

7. A lubricating oil containing a monocarbonate represented by the following general formula [II] and a monocarbonate represented by the following general formula [III];

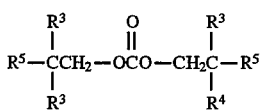
[II]

wherein $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 20 carbon atoms.

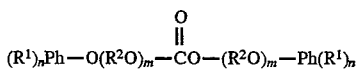
[III]

wherein $R^1$ stands each independently for a hydrocarbon group having 1 to 20 carbon atoms an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands each independently for an aromatic substituent, n stands independently for an integer of from 1 to 5, and m stands independently for an integer of from 1 to 30.

8. A lubricating oil according to claim 7, wherein said lubricating oil is used for refrigerators.

9. A lubricating oil for refrigerator use according to claim 8, wherein said lubricating oil further contains a hydrogenated fluorocarbon.

10. A process for the preparation of a composition comprising monocarbonates represented by the following general formulae [I], [II] and [III],

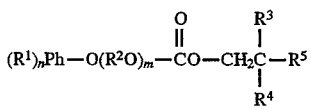
[I]

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 30 carbon atoms, Ph stands for an aromatic substituent, n stands for an integer of from 1 to 5, and m stands for an integer of from 1 to 30,

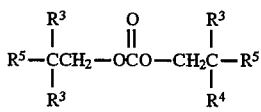
[II]

wherein $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 20 carbon atoms,

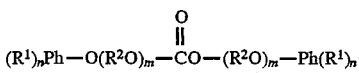
[III]

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms, or a halogen-substituted hydrocarbon group having 1 to 10 carbon atoms, $R^2$ stands each independently for an alkylene group having 2 to 4 carbon atoms, Ph stands each independently for an aromatic substituent, n stands each independently for an integer of from 1 to 5, and m stands each independently for an integer of from 1 to 30, said process comprising the steps of:
providing a mixture of (a) a monoalcohol having aromatic ring which is represented by the general formula [IV]

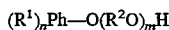
[IV]

wherein $R^1$ stands each independently for a hydrocarbon group having 1 to 20 carbon atoms, an alkoxyl group having 1 to 12 carbon atoms, an etheric oxygen-containing hydrocarbon group having 2 to 30 carbon atoms or a halogen-substituted hydrocarbon group having 1 to 10 carbon atoms, $R^2$ stands each independently for an alkylene group having 2 to 4 carbon atoms, Ph stands for an aromatic substituent, n stands for an integer of from 1 to 5, and m stands for an integer of from 1 to 30, (b) a monoalcohol which is represented by the general formula [V];

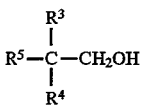
[V]

wherein $R^3$, $R^4$ and $R^5$, which may be same or different, stand for a hydrocarbon group having 1 to 20 carbon atoms, an alkoxyl group having 1 to 12 carbon atoms or an etheric oxygen-containing hydrocarbon group having 2 to 30 carbon atoms, and (c) a monocarbonate which is represented by the general formula [VI];

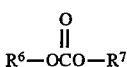
[VI]

wherein $R^6$ and $R^7$, which may be same or different, stand for a hydrocarbon group having 1 to 8 carbon atoms or an etheric oxygen-containing hydrocarbon group having 2 to 18 carbon atoms, heating the mixture so as to remove $R^6OH$ and/or $R^7OH$ from the mixture by alcoholysis reaction which forms a monocarbonate composition.

* * * * *